(12) United States Patent
Hunter et al.

(10) Patent No.: US 8,271,203 B2
(45) Date of Patent: *Sep. 18, 2012

(54) METHODS AND SYSTEMS FOR SEQUENCE-BASED DESIGN OF MULTIPLE REACTION MONITORING TRANSITIONS AND EXPERIMENTS

(75) Inventors: Christie L. Hunter, San Mateo, CA (US); Alpesh A. Patel, San Francisco, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 746 days.

This patent is subject to a terminal disclaimer.

(21) Appl. No.: 11/777,248

(22) Filed: Jul. 12, 2007

(65) Prior Publication Data

US 2008/0021687 A1    Jan. 24, 2008

Related U.S. Application Data

(60) Provisional application No. 60/807,100, filed on Jul. 12, 2006, provisional application No. 60/932,730, filed on Jun. 2, 2007.

(51) Int. Cl.
  *G06G 7/58* (2006.01)
  *G06F 19/00* (2006.01)
(52) U.S. Cl. .......... 702/19; 703/11; 250/282; 435/5
(58) Field of Classification Search .......... None
  See application file for complete search history.

(56) References Cited

U.S. PATENT DOCUMENTS

| | | | | |
|---|---|---|---|---|
| 6,891,154 B2 * | 5/2005 | Zhu et al. | .......... | 250/282 |
| 2006/0287834 A1 * | 12/2006 | Kearney et al. | .......... | 702/27 |

FOREIGN PATENT DOCUMENTS
WO    WO 01/97251 A    12/2001

OTHER PUBLICATIONS

Geer et al. Journal of Proteome Research 2004, 3, 958-964.*
Perkins et al. Electrophoresis, 1999, 20, 3551-3567.*
Anderson, Leigh et al.: "Quantitative mass spectrometric multiple reaction monitoring assays for major plasma proteins" Molecular & Cellular Proteomics, ASBBM, Birminham, AL US, vol. 5, No. 4, Apr. 2006, pp. 573-588 see figure 8.
Unwin, Richard D. et al.: "Multiple reaction monitoring to identify sites of protein phosphorylation with high sensitivity" Molecular & Cellular Proteomics, ASBBM, Birmingham, AL, US, vol. 4, No. 8, Aug. 2005 pp. 1134-1144 see abstract, figures 1,4.
Savitski, Mikhail M et al.: "New data base-independent, sequence tag-based scoring of peptide MS/MS data validates Mowse scores, recovers below threshold data, singles out modified peptides, and assesses the quality of MS/MS techniques", Molecular & Cellular Proteomics, ASBBM, Birmingham, AL, US, vol. 4, No. 8, Aug. 2005, pp. 1180-1188 see entire document.
Cox David M et al.: "Multiple reaction monitoring as a method for identifying protein posttranslational modifications," Journal of Biomolecular Techniques, Association of Biomolecular Resource Facilities, Santa Fe, NM, US, vol. 16, No. 2, Jun. 2005, pp. 83-90, see abstract, p. 84, left-hand column, In 1-24, p. 85, left-hand column, In. 17—right-hand column, line 15, figure 1-2.

* cited by examiner

*Primary Examiner* — Michael Borin
(74) *Attorney, Agent, or Firm* — John R. Kasha; Kasha Law LLC

(57)   ABSTRACT

Computer-implementable methods consistent with the present teachings can be used in the design of selective- and multiple-reaction monitoring experiments for the identification of proteins and peptides of interest. By determining candidate parent-daughter ion transition pairs and scoring the pairs based on their ability to be detected experimental design time can be reduced and with a more focused list of transition pairs more experiments can be run successfully in a given period of time.

17 Claims, 12 Drawing Sheets

Figure 5

| Peptide Sequence | MW | Type | Index | Charge | Q1 | Q3 | P(detection) |
|---|---|---|---|---|---|---|---|
| PHSHPALTPEQK | 1340.686 | b | 2 | 3 | 447.9 | 235.1 | 0.127 |
| PHSHPALTPEQK | 1340.686 | b | 4 | 3 | 447.9 | 459.2 | 0.157 |
| PHSHPALTPEQK | 1340.686 | b | 6 | 3 | 447.9 | 627.3 | 0.106 |
| PHSHPALTPEQK | 1340.686 | b | 8 | 3 | 447.9 | 841.4 | 0.135 |
| PHSHPALTPEQK | 1340.686 | y | 10 | 3 | 447.9 | 1107.6 | 0.111 |
| PHSHPALTPEQK | 1340.686 | y | 8 | 3 | 447.9 | 883.5 | 0.155 |
| PHSHPALTPEQK | 1340.686 | y | 7 | 3 | 447.9 | 786.4 | 0.076 |
| PHSHPALTPEQK | 1340.686 | y | 5 | 3 | 447.9 | 602.3 | 0.117 |
| ELSDIAHR | 939.478 | b | 1 | 2 | 470.7 | 130.1 | 0.024 |
| ELSDIAHR | 939.478 | b | 2 | 2 | 470.7 | 243.1 | 0.135 |
| ELSDIAHR | 939.478 | b | 5 | 2 | 470.7 | 558.3 | 0.027 |
| ELSDIAHR | 939.478 | b | 6 | 2 | 470.7 | 629.3 | 0.026 |
| ELSDIAHR | 939.478 | y | 7 | 2 | 470.7 | 811.4 | 0.109 |
| ELSDIAHR | 939.478 | y | 5 | 2 | 470.7 | 611.3 | 0.087 |
| ELSDIAHR | 939.478 | y | 4 | 2 | 470.7 | 496.3 | 0.128 |
| ELSDIAHR | 939.478 | y | 1 | 2 | 470.7 | 175.1 | 0.078 |
| IVAPGK | 583.369 | b | 2 | 1 | 584.4 | 213.2 | 0.130 |
| IVAPGK | 583.369 | b | 3 | 1 | 584.4 | 284.2 | 0.030 |
| IVAPGK | 583.369 | b | 4 | 1 | 584.4 | 381.3 | 0.018 |
| IVAPGK | 583.369 | b | 5 | 1 | 584.4 | 438.3 | 0.015 |
| IVAPGK | 583.369 | y | 5 | 1 | 584.4 | 471.3 | 0.111 |
| IVAPGK | 583.369 | y | 2 | 1 | 584.4 | 204.1 | 0.080 |
| IVAPGKGILAADESTGSIAK | 1897.051 | b | 2 | 3 | 633.4 | 213.2 | 0.012 |
| IVAPGKGILAADESTGSIAK | 1897.051 | b | 15 | 3 | 633.4 | 1423.8 | 0.002 |
| IVAPGKGILAADESTGSIAK | 1897.051 | b | 17 | 3 | 633.4 | 1567.8 | 0.001 |
| IVAPGKGILAADESTGSIAK | 1897.051 | b | 18 | 3 | 633.4 | 1680.9 | 0.000 |
| IVAPGKGILAADESTGSIAK | 1897.051 | y | 19 | 3 | 633.4 | 1785 | 0.000 |
| IVAPGKGILAADESTGSIAK | 1897.051 | y | 17 | 3 | 633.4 | 1614.9 | 0.001 |
| IVAPGKGILAADESTGSIAK | 1897.051 | y | 9 | 3 | 633.4 | 907.4 | 0.009 |
| IVAPGKGILAADESTGSIAK | 1897.051 | y | 8 | 3 | 633.4 | 792.4 | 0.009 |
| IVAPGKGILAADESTGSIAK | 1897.051 | b | 2 | 2 | 949.5 | 213.2 | 0.006 |
| IVAPGKGILAADESTGSIAK | 1897.051 | b | 3 | 2 | 949.5 | 284.2 | 0.001 |
| IVAPGKGILAADESTGSIAK | 1897.051 | b | 7 | 2 | 949.5 | 623.4 | 0.004 |
| IVAPGKGILAADESTGSIAK | 1897.051 | b | 8 | 2 | 949.5 | 736.5 | 0.005 |
| IVAPGKGILAADESTGSIAK | 1897.051 | y | 17 | 2 | 949.5 | 1614.9 | 0.000 |
| IVAPGKGILAADESTGSIAK | 1897.051 | y | 11 | 2 | 949.5 | 1049.5 | 0.005 |
| IVAPGKGILAADESTGSIAK | 1897.051 | y | 8 | 2 | 949.5 | 792.4 | 0.006 |
| IVAPGKGILAADESTGSIAK | 1897.051 | y | 3 | 2 | 949.5 | 331.2 | 0.004 |
| GILAADESTGSIAK | 1331.693 | b | 2 | 2 | 666.9 | 171.1 | 0.056 |
| GILAADESTGSIAK | 1331.693 | b | 8 | 2 | 666.9 | 757.4 | 0.009 |
| GILAADESTGSIAK | 1331.693 | b | 9 | 2 | 666.9 | 858.4 | 0.010 |
| GILAADESTGSIAK | 1331.693 | b | 13 | 2 | 666.9 | 1186.6 | 0.004 |
| GILAADESTGSIAK | 1331.693 | y | 11 | 2 | 666.9 | 1049.5 | 0.046 |

Figure 5

| Peptide | Mass | Ion | # | Charge | Q1 | Q3 | Intensity |
|---|---|---|---|---|---|---|---|
| GILAADESTGSIAK | 1331.693 | y | 9 | 2 | 666.9 | 907.4 | 0.043 |
| GILAADESTGSIAK | 1331.693 | y | 8 | 2 | 666.9 | 792.4 | 0.042 |
| GILAADESTGSIAK | 1331.693 | y | 6 | 2 | 666.9 | 576.3 | 0.039 |
| GILAADESTGSIAKR | 1487.794 | b | 1 | 3 | 496.9 | 58 | 0.028 |
| GILAADESTGSIAKR | 1487.794 | b | 2 | 3 | 496.9 | 171.1 | 0.200 |
| GILAADESTGSIAKR | 1487.794 | b | 6 | 3 | 496.9 | 541.3 | 0.036 |
| GILAADESTGSIAKR | 1487.794 | b | 13 | 3 | 496.9 | 1186.6 | 0.015 |
| GILAADESTGSIAKR | 1487.794 | y | 13 | 3 | 496.9 | 1318.7 | 0.083 |
| GILAADESTGSIAKR | 1487.794 | y | 9 | 3 | 496.9 | 948.5 | 0.148 |
| GILAADESTGSIAKR | 1487.794 | y | 8 | 3 | 496.9 | 819.5 | 0.179 |
| GILAADESTGSIAKR | 1487.794 | y | 6 | 3 | 496.9 | 631.4 | 0.172 |
| GILAADESTGSIAKR | 1487.794 | b | 2 | 2 | 744.9 | 171.1 | 0.100 |
| GILAADESTGSIAKR | 1487.794 | b | 5 | 2 | 744.9 | 426.3 | 0.020 |
| GILAADESTGSIAKR | 1487.794 | b | 6 | 2 | 744.9 | 541.3 | 0.024 |
| GILAADESTGSIAKR | 1487.794 | b | 12 | 2 | 744.9 | 1115.6 | 0.017 |
| GILAADESTGSIAKR | 1487.794 | y | 12 | 2 | 744.9 | 1205.6 | 0.066 |
| GILAADESTGSIAKR | 1487.794 | y | 9 | 2 | 744.9 | 948.5 | 0.097 |
| GILAADESTGSIAKR | 1487.794 | y | 8 | 2 | 744.9 | 819.5 | 0.095 |
| GILAADESTGSIAKR | 1487.794 | y | 5 | 2 | 744.9 | 574.4 | 0.072 |
| RLQSIGTENTEENR | 1645.804 | b | 2 | 3 | 549.6 | 270.2 | 0.001 |
| RLQSIGTENTEENR | 1645.804 | b | 5 | 3 | 549.6 | 598.4 | 0.001 |
| RLQSIGTENTEENR | 1645.804 | b | 6 | 3 | 549.6 | 655.4 | 0.001 |
| RLQSIGTENTEENR | 1645.804 | b | 10 | 3 | 549.6 | 1100.6 | 0.001 |
| RLQSIGTENTEENR | 1645.804 | y | 12 | 3 | 549.6 | 1377.6 | 0.000 |
| RLQSIGTENTEENR | 1645.804 | y | 6 | 3 | 549.6 | 762.3 | 0.001 |
| RLQSIGTENTEENR | 1645.804 | y | 3 | 3 | 549.6 | 418.2 | 0.001 |
| LQSIGTENTEENR | 1489.703 | b | 2 | 2 | 745.9 | 242.2 | 0.060 |
| LQSIGTENTEENR | 1489.703 | b | 3 | 2 | 745.9 | 329.2 | 0.010 |
| LQSIGTENTEENR | 1489.703 | b | 10 | 2 | 745.9 | 1073.5 | 0.010 |
| LQSIGTENTEENR | 1489.703 | b | 11 | 2 | 745.9 | 1202.6 | 0.009 |
| LQSIGTENTEENR | 1489.703 | y | 11 | 2 | 745.9 | 1249.6 | 0.034 |
| LQSIGTENTEENR | 1489.703 | y | 7 | 2 | 745.9 | 891.4 | 0.045 |
| LQSIGTENTEENR | 1489.703 | y | 6 | 2 | 745.9 | 762.3 | 0.052 |
| LQSIGTENTEENR | 1489.703 | y | 2 | 2 | 745.9 | 289.2 | 0.053 |
| LQSIGTENTEENRR | 1645.804 | b | 2 | 3 | 549.6 | 242.2 | 0.200 |
| LQSIGTENTEENRR | 1645.804 | b | 4 | 3 | 549.6 | 442.3 | 0.048 |
| LQSIGTENTEENRR | 1645.804 | b | 8 | 3 | 549.6 | 843.4 | 0.040 |
| LQSIGTENTEENRR | 1645.804 | b | 10 | 3 | 549.6 | 1073.5 | 0.036 |
| LQSIGTENTEENRR | 1645.804 | y | 7 | 3 | 549.6 | 918.4 | 0.188 |
| LQSIGTENTEENRR | 1645.804 | y | 5 | 3 | 549.6 | 703.4 | 0.168 |
| LQSIGTENTEENRR | 1645.804 | y | 2 | 3 | 549.6 | 331.2 | 0.088 |
| LQSIGTENTEENRR | 1645.804 | y | 1 | 3 | 549.6 | 175.1 | 0.064 |
| FYR | 484.243 | b | 1 | 1 | 485.3 | 148.1 | 0.026 |
| FYR | 484.243 | b | 2 | 1 | 485.3 | 311.1 | 0.100 |
| FYR | 484.243 | y | 2 | 1 | 485.3 | 338.2 | 0.116 |

Figure 5

| | | | | | | | |
|---|---|---|---|---|---|---|---|
| FYR | 484.243 | y | 1 | 1 | 485.3 | 175.1 | 0.092 |
| FYRQLLLTADDR | 1509.794 | b | 2 | 3 | 504.3 | 311.1 | 0.015 |
| FYRQLLLTADDR | 1509.794 | b | 7 | 3 | 504.3 | 934.6 | 0.024 |
| FYRQLLLTADDR | 1509.794 | b | 8 | 3 | 504.3 | 1035.6 | 0.021 |
| FYRQLLLTADDR | 1509.794 | b | 11 | 3 | 504.3 | 1336.7 | 0.005 |
| FYRQLLLTADDR | 1509.794 | y | 6 | 3 | 504.3 | 690.3 | 0.025 |
| FYRQLLLTADDR | 1509.794 | y | 5 | 3 | 504.3 | 577.3 | 0.025 |
| FYRQLLLTADDR | 1509.794 | y | 3 | 3 | 504.3 | 405.2 | 0.022 |
| FYRQLLLTADDR | 1509.794 | y | 2 | 3 | 504.3 | 290.1 | 0.022 |
| QLLLTADDR | 1043.562 | b | 1 | 2 | 522.8 | 129.1 | 0.050 |
| QLLLTADDR | 1043.562 | b | 2 | 2 | 522.8 | 242.2 | 0.275 |
| QLLLTADDR | 1043.562 | b | 5 | 2 | 522.8 | 569.4 | 0.048 |
| QLLLTADDR | 1043.562 | b | 6 | 2 | 522.8 | 640.4 | 0.050 |
| QLLLTADDR | 1043.562 | y | 7 | 2 | 522.8 | 803.4 | 0.245 |
| QLLLTADDR | 1043.562 | y | 6 | 2 | 522.8 | 690.3 | 0.246 |
| QLLLTADDR | 1043.562 | y | 5 | 2 | 522.8 | 577.3 | 0.251 |
| QLLLTADDR | 1043.562 | y | 4 | 2 | 522.8 | 476.2 | 0.216 |
| QLLLTADDR | 1043.562 | b | 2 | 1 | 1044.6 | 242.2 | 0.115 |
| QLLLTADDR | 1043.562 | b | 3 | 1 | 1044.6 | 355.2 | 0.023 |
| QLLLTADDR | 1043.562 | b | 5 | 1 | 1044.6 | 569.4 | 0.022 |
| QLLLTADDR | 1043.562 | b | 8 | 1 | 1044.6 | 870.5 | 0.037 |
| QLLLTADDR | 1043.562 | y | 8 | 1 | 1044.6 | 916.5 | 0.096 |
| QLLLTADDR | 1043.562 | y | 7 | 1 | 1044.6 | 803.4 | 0.103 |
| QLLLTADDRVNPCIGGVILFHETLYQK | 3112.638 | b | 2 | 4 | 779.2 | 242.2 | 0.025 |
| QLLLTADDRVNPCIGGVILFHETLYQK | 3112.638 | b | 5 | 4 | 779.2 | 569.4 | 0.004 |
| QLLLTADDRVNPCIGGVILFHETLYQK | 3112.638 | b | 21 | 4 | 779.2 | 2333.2 | 0.000 |
| QLLLTADDRVNPCIGGVILFHETLYQK | 3112.638 | y | 16 | 4 | 779.2 | 1875 | 0.000 |
| QLLLTADDRVNPCIGGVILFHETLYQK | 3112.638 | y | 8 | 4 | 779.2 | 1065.5 | 0.020 |
| QLLLTADDRVNPCIGGVILFHETLYQK | 3112.638 | y | 7 | 4 | 779.2 | 918.5 | 0.015 |
| QLLLTADDRVNPCIGGVILFHETLYQK | 3112.638 | y | 3 | 4 | 779.2 | 438.2 | 0.022 |
| VNPCIGGVILFHETLYQK | 2087.087 | b | 1 | 3 | 696.7 | 100.1 | 0.049 |
| VNPCIGGVILFHETLYQK | 2087.087 | b | 2 | 3 | 696.7 | 214.1 | 0.280 |
| VNPCIGGVILFHETLYQK | 2087.087 | b | 7 | 3 | 696.7 | 698.3 | 0.031 |
| VNPCIGGVILFHETLYQK | 2087.087 | b | 11 | 3 | 696.7 | 1170.6 | 0.025 |
| VNPCIGGVILFHETLYQK | 2087.087 | y | 16 | 3 | 696.7 | 1875 | 0.001 |
| VNPCIGGVILFHETLYQK | 2087.087 | y | 9 | 3 | 696.7 | 1178.6 | 0.167 |
| VNPCIGGVILFHETLYQK | 2087.087 | y | 7 | 3 | 696.7 | 918.5 | 0.143 |
| VNPCIGGVILFHETLYQK | 2087.087 | y | 6 | 3 | 696.7 | 781.4 | 0.117 |
| VNPCIGGVILFHETLYQK | 2087.087 | b | 2 | 2 | 1044.6 | 214.1 | 0.145 |
| VNPCIGGVILFHETLYQK | 2087.087 | b | 10 | 2 | 1044.6 | 1023.6 | 0.024 |
| VNPCIGGVILFHETLYQK | 2087.087 | b | 11 | 2 | 1044.6 | 1170.6 | 0.019 |
| VNPCIGGVILFHETLYQK | 2087.087 | b | 12 | 2 | 1044.6 | 1307.7 | 0.053 |
| VNPCIGGVILFHETLYQK | 2087.087 | y | 16 | 2 | 1044.6 | 1875 | 0.000 |
| VNPCIGGVILFHETLYQK | 2087.087 | y | 13 | 2 | 1044.6 | 1504.8 | 0.014 |
| VNPCIGGVILFHETLYQK | 2087.087 | y | 9 | 2 | 1044.6 | 1178.6 | 0.086 |

Figure 5

| Peptide | Mass | Ion | # | Charge | Q1 | Q3 | Intensity |
|---|---|---|---|---|---|---|---|
| VNPCIGGVILFHETLYQK | 2087.087 | y | 5 | 2 | 1044.6 | 652.4 | 0.108 |
| VNPCIGGVILFHETLYQKADDGRPFPQVIK | 3410.78 | b | 2 | 5 | 683.2 | 214.1 | 0.050 |
| VNPCIGGVILFHETLYQKADDGRPFPQVIK | 3410.78 | b | 4 | 5 | 683.2 | 471.2 | 0.008 |
| VNPCIGGVILFHETLYQKADDGRPFPQVIK | 3410.78 | b | 9 | 5 | 683.2 | 910.5 | 0.009 |
| VNPCIGGVILFHETLYQKADDGRPFPQVIK | 3410.78 | b | 19 | 5 | 683.2 | 2141.1 | 0.000 |
| VNPCIGGVILFHETLYQKADDGRPFPQVIK | 3410.78 | y | 7 | 5 | 683.2 | 828.5 | 0.038 |
| VNPCIGGVILFHETLYQKADDGRPFPQVIK | 3410.78 | y | 4 | 5 | 683.2 | 487.3 | 0.020 |
| VNPCIGGVILFHETLYQKADDGRPFPQVIK | 3410.78 | b | 2 | 4 | 853.7 | 214.1 | 0.025 |
| VNPCIGGVILFHETLYQKADDGRPFPQVIK | 3410.78 | b | 7 | 4 | 853.7 | 698.3 | 0.003 |
| VNPCIGGVILFHETLYQKADDGRPFPQVIK | 3410.78 | b | 13 | 4 | 853.7 | 1436.7 | 0.004 |
| VNPCIGGVILFHETLYQKADDGRPFPQVIK | 3410.78 | b | 19 | 4 | 853.7 | 2141.1 | 0.000 |
| VNPCIGGVILFHETLYQKADDGRPFPQVIK | 3410.78 | y | 18 | 4 | 853.7 | 2105.1 | 0.000 |
| VNPCIGGVILFHETLYQKADDGRPFPQVIK | 3410.78 | y | 9 | 4 | 853.7 | 1041.6 | 0.022 |
| VNPCIGGVILFHETLYQKADDGRPFPQVIK | 3410.78 | y | 4 | 4 | 853.7 | 487.3 | 0.012 |
| ADDGRPFPQVIK | 1341.704 | b | 2 | 3 | 448.2 | 187.1 | 0.175 |
| ADDGRPFPQVIK | 1341.704 | b | 5 | 3 | 448.2 | 515.2 | 0.177 |
| ADDGRPFPQVIK | 1341.704 | b | 9 | 3 | 448.2 | 984.5 | 0.151 |
| ADDGRPFPQVIK | 1341.704 | b | 11 | 3 | 448.2 | 1196.6 | 0.078 |
| ADDGRPFPQVIK | 1341.704 | y | 7 | 3 | 448.2 | 828.5 | 0.175 |
| ADDGRPFPQVIK | 1341.704 | y | 5 | 3 | 448.2 | 584.4 | 0.225 |
| ADDGRPFPQVIK | 1341.704 | y | 3 | 3 | 448.2 | 359.3 | 0.157 |
| ADDGRPFPQVIK | 1341.704 | b | 2 | 2 | 671.9 | 187.1 | 0.110 |
| ADDGRPFPQVIK | 1341.704 | b | 3 | 2 | 671.9 | 302.1 | 0.025 |
| ADDGRPFPQVIK | 1341.704 | b | 7 | 2 | 671.9 | 759.3 | 0.114 |
| ADDGRPFPQVIK | 1341.704 | b | 10 | 2 | 671.9 | 1083.5 | 0.085 |
| ADDGRPFPQVIK | 1341.704 | y | 11 | 2 | 671.9 | 1271.7 | 0.046 |
| ADDGRPFPQVIK | 1341.704 | y | 10 | 2 | 671.9 | 1156.6 | 0.080 |
| ADDGRPFPQVIK | 1341.704 | y | 7 | 2 | 671.9 | 828.5 | 0.107 |
| ADDGRPFPQVIKSK | 1556.831 | b | 2 | 3 | 520 | 187.1 | 0.020 |
| ADDGRPFPQVIKSK | 1556.831 | b | 6 | 3 | 520 | 612.3 | 0.013 |
| ADDGRPFPQVIKSK | 1556.831 | b | 11 | 3 | 520 | 1196.6 | 0.013 |
| ADDGRPFPQVIKSK | 1556.831 | b | 12 | 3 | 520 | 1324.7 | 0.009 |
| ADDGRPFPQVIKSK | 1556.831 | y | 13 | 3 | 520 | 1486.8 | 0.002 |
| ADDGRPFPQVIKSK | 1556.831 | y | 7 | 3 | 520 | 799.5 | 0.023 |
| ADDGRPFPQVIKSK | 1556.831 | y | 6 | 3 | 520 | 702.5 | 0.011 |
| ADDGRPFPQVIKSK | 1556.831 | y | 1 | 3 | 520 | 147.1 | 0.013 |
| SKGGVVGIK | 843.516 | b | 2 | 2 | 422.8 | 216.1 | 0.023 |
| SKGGVVGIK | 843.516 | b | 4 | 2 | 422.8 | 330.2 | 0.014 |
| SKGGVVGIK | 843.516 | b | 6 | 2 | 422.8 | 528.3 | 0.023 |
| SKGGVVGIK | 843.516 | b | 8 | 2 | 422.8 | 698.4 | 0.019 |
| SKGGVVGIK | 843.516 | y | 6 | 2 | 422.8 | 572.4 | 0.016 |
| SKGGVVGIK | 843.516 | y | 5 | 2 | 422.8 | 515.4 | 0.014 |
| SKGGVVGIK | 843.516 | y | 3 | 2 | 422.8 | 317.2 | 0.023 |
| SKGGVVGIK | 843.516 | y | 2 | 2 | 422.8 | 260.2 | 0.014 |
| GGVVGIK | 628.389 | b | 1 | 1 | 629.4 | 58 | 0.018 |

Figure 5

| Peptide | Mass | Ion | # | Charge | m/z | Frag | Intensity |
|---|---|---|---|---|---|---|---|
| GGVVGIK | 628.389 | b | 2 | 1 | 629.4 | 115.1 | 0.080 |
| GGVVGIK | 628.389 | b | 3 | 1 | 629.4 | 214.1 | 0.023 |
| GGVVGIK | 628.389 | b | 5 | 1 | 629.4 | 370.2 | 0.016 |
| GGVVGIK | 628.389 | y | 4 | 1 | 629.4 | 416.3 | 0.104 |
| GGVVGIK | 628.389 | y | 3 | 1 | 629.4 | 317.2 | 0.116 |
| GGVVGIKVDK | 970.579 | b | 2 | 2 | 486.3 | 115.1 | 0.015 |
| GGVVGIKVDK | 970.579 | b | 4 | 2 | 486.3 | 313.2 | 0.005 |
| GGVVGIKVDK | 970.579 | b | 6 | 2 | 486.3 | 483.3 | 0.004 |
| GGVVGIKVDK | 970.579 | b | 9 | 2 | 486.3 | 825.5 | 0.021 |
| GGVVGIKVDK | 970.579 | y | 7 | 2 | 486.3 | 758.5 | 0.021 |
| GGVVGIKVDK | 970.579 | y | 5 | 2 | 486.3 | 602.4 | 0.014 |
| GGVVGIKVDK | 970.579 | y | 4 | 2 | 486.3 | 489.3 | 0.019 |
| GGVVGIKVDK | 970.579 | y | 3 | 2 | 486.3 | 361.2 | 0.020 |
| VDKGVVPLAGTNGETTTQGLDGLSER | 2613.324 | b | 2 | 3 | 872.1 | 215.1 | 0.020 |
| VDKGVVPLAGTNGETTTQGLDGLSER | 2613.324 | b | 4 | 3 | 872.1 | 400.2 | 0.027 |
| VDKGVVPLAGTNGETTTQGLDGLSER | 2613.324 | b | 20 | 3 | 872.1 | 1939 | 0.000 |
| VDKGVVPLAGTNGETTTQGLDGLSER | 2613.324 | b | 21 | 3 | 872.1 | 2054 | 0.000 |
| VDKGVVPLAGTNGETTTQGLDGLSER | 2613.324 | y | 25 | 3 | 872.1 | 2515.3 | 0.000 |
| VDKGVVPLAGTNGETTTQGLDGLSER | 2613.324 | y | 20 | 3 | 872.1 | 2017 | 0.000 |
| VDKGVVPLAGTNGETTTQGLDGLSER | 2613.324 | y | 16 | 3 | 872.1 | 1678.8 | 0.001 |
| VDKGVVPLAGTNGETTTQGLDGLSER | 2613.324 | y | 10 | 3 | 872.1 | 1075.5 | 0.033 |
| GVVPLAGTNGETTTQGLDGLSER | 2271.134 | b | 2 | 2 | 1136.6 | 157.1 | 0.235 |
| GVVPLAGTNGETTTQGLDGLSER | 2271.134 | b | 4 | 2 | 1136.6 | 353.2 | 0.026 |
| GVVPLAGTNGETTTQGLDGLSER | 2271.134 | b | 17 | 2 | 1136.6 | 1596.8 | 0.002 |
| GVVPLAGTNGETTTQGLDGLSER | 2271.134 | b | 22 | 2 | 1136.6 | 2098 | 0.000 |
| GVVPLAGTNGETTTQGLDGLSER | 2271.134 | y | 20 | 2 | 1136.6 | 2017 | 0.000 |
| GVVPLAGTNGETTTQGLDGLSER | 2271.134 | y | 12 | 2 | 1136.6 | 1277.6 | 0.111 |
| GVVPLAGTNGETTTQGLDGLSER | 2271.134 | y | 8 | 2 | 1136.6 | 846.4 | 0.211 |
| GVVPLAGTNGETTTQGLDGLSER | 2271.134 | y | 3 | 2 | 1136.6 | 391.2 | 0.225 |
| GVVPLAGTNGETTTQGLDGLSERCAQYK | 2921.419 | b | 2 | 3 | 974.8 | 157.1 | 0.020 |
| GVVPLAGTNGETTTQGLDGLSERCAQYK | 2921.419 | b | 7 | 3 | 974.8 | 594.4 | 0.003 |
| GVVPLAGTNGETTTQGLDGLSERCAQYK | 2921.419 | b | 9 | 3 | 974.8 | 809.5 | 0.004 |
| GVVPLAGTNGETTTQGLDGLSERCAQYK | 2921.419 | b | 18 | 3 | 974.8 | 1711.8 | 0.000 |
| GVVPLAGTNGETTTQGLDGLSERCAQYK | 2921.419 | y | 25 | 3 | 974.8 | 2667.3 | 0.000 |
| GVVPLAGTNGETTTQGLDGLSERCAQYK | 2921.419 | y | 21 | 3 | 974.8 | 2329.1 | 0.000 |
| GVVPLAGTNGETTTQGLDGLSERCAQYK | 2921.419 | y | 9 | 3 | 974.8 | 1154.6 | 0.010 |
| GVVPLAGTNGETTTQGLDGLSERCAQYK | 2921.419 | y | 2 | 3 | 974.8 | 310.2 | 0.018 |
| CAQYK | 668.296 | b | 1 | 1 | 669.3 | 161 | 0.005 |
| CAQYK | 668.296 | b | 2 | 1 | 669.3 | 232.1 | 0.027 |
| CAQYK | 668.296 | b | 3 | 1 | 669.3 | 360.1 | 0.006 |
| CAQYK | 668.296 | b | 4 | 1 | 669.3 | 523.2 | 0.005 |
| CAQYK | 668.296 | y | 4 | 1 | 669.3 | 509.3 | 0.021 |
| CAQYK | 668.296 | y | 3 | 1 | 669.3 | 438.2 | 0.025 |
| KDGADFAK | 850.418 | b | 2 | 2 | 426.2 | 244.1 | 0.006 |
| KDGADFAK | 850.418 | b | 3 | 2 | 426.2 | 301.2 | 0.004 |

Figure 5

| | | | | | | | |
|---|---|---|---|---|---|---|---|
| KDGADFAK | | 850.418 | b | 4 | 2 | 426.2 | 372.2 | 0.004 |
| KDGADFAK | | 850.418 | b | 6 | 2 | 426.2 | 634.3 | 0.005 |
| KDGADFAK | | 850.418 | y | 7 | 2 | 426.2 | 723.3 | 0.005 |
| KDGADFAK | | 850.418 | y | 6 | 2 | 426.2 | 608.3 | 0.006 |
| KDGADFAK | | 850.418 | y | 5 | 2 | 426.2 | 551.3 | 0.004 |
| KDGADFAK | | 850.418 | y | 4 | 2 | 426.2 | 480.2 | 0.004 |
| DGADFAK | | 722.323 | b | 1 | 1 | 723.3 | 116 | 0.027 |
| DGADFAK | | 722.323 | b | 2 | 1 | 723.3 | 173.1 | 0.080 |
| DGADFAK | | 722.323 | b | 5 | 1 | 723.3 | 506.2 | 0.021 |
| DGADFAK | | 722.323 | b | 6 | 1 | 723.3 | 577.2 | 0.019 |
| DGADFAK | | 722.323 | y | 6 | 1 | 723.3 | 608.3 | 0.124 |
| DGADFAK | | 722.323 | y | 3 | 1 | 723.3 | 365.2 | 0.119 |
| DGADFAK | | 722.323 | y | 1 | 1 | 723.3 | 147.1 | 0.083 |
| DGADFAKWR | | 1064.503 | b | 2 | 2 | 533.3 | 173.1 | 0.020 |
| DGADFAKWR | | 1064.503 | b | 4 | 2 | 533.3 | 359.1 | 0.006 |
| DGADFAKWR | | 1064.503 | b | 6 | 2 | 533.3 | 577.2 | 0.004 |
| DGADFAKWR | | 1064.503 | b | 8 | 2 | 533.3 | 891.4 | 0.014 |
| DGADFAKWR | | 1064.503 | y | 7 | 2 | 533.3 | 893.5 | 0.017 |
| DGADFAKWR | | 1064.503 | y | 5 | 2 | 533.3 | 707.4 | 0.027 |
| DGADFAKWR | | 1064.503 | y | 4 | 2 | 533.3 | 560.3 | 0.021 |
| CVLK | | 518.289 | b | 1 | 1 | 519.3 | 161 | 0.018 |
| CVLK | | 518.289 | b | 2 | 1 | 519.3 | 260.1 | 0.130 |
| CVLK | | 518.289 | b | 3 | 1 | 519.3 | 373.2 | 0.023 |
| CVLK | | 518.289 | y | 3 | 1 | 519.3 | 359.3 | 0.079 |
| CVLK | | 518.289 | y | 1 | 1 | 519.3 | 147.1 | 0.102 |
| CVLKIGEHTPSALAIMENANVLAR | | 2606.367 | b | 2 | 4 | 652.6 | 260.1 | 0.055 |
| CVLKIGEHTPSALAIMENANVLAR | | 2606.367 | b | 11 | 4 | 652.6 | 1222.6 | 0.026 |
| CVLKIGEHTPSALAIMENANVLAR | | 2606.367 | b | 16 | 4 | 652.6 | 1721.9 | 0.001 |
| CVLKIGEHTPSALAIMENANVLAR | | 2606.367 | b | 21 | 4 | 652.6 | 2249.1 | 0.000 |
| CVLKIGEHTPSALAIMENANVLAR | | 2606.367 | y | 15 | 4 | 652.6 | 1569.8 | 0.004 |
| CVLKIGEHTPSALAIMENANVLAR | | 2606.367 | y | 8 | 4 | 652.6 | 886.5 | 0.038 |
| CVLKIGEHTPSALAIMENANVLAR | | 2606.367 | y | 6 | 4 | 652.6 | 643.4 | 0.040 |
| CVLKIGEHTPSALAIMENANVLAR | | 2606.367 | y | 2 | 4 | 652.6 | 246.2 | 0.047 |
| CVLKIGEHTPSALAIMENANVLAR | | 2606.367 | b | 2 | 3 | 869.8 | 260.1 | 0.030 |
| CVLKIGEHTPSALAIMENANVLAR | | 2606.367 | b | 4 | 3 | 869.8 | 501.3 | 0.025 |
| CVLKIGEHTPSALAIMENANVLAR | | 2606.367 | b | 20 | 3 | 869.8 | 2150.1 | 0.000 |
| CVLKIGEHTPSALAIMENANVLAR | | 2606.367 | b | 21 | 3 | 869.8 | 2249.1 | 0.000 |
| CVLKIGEHTPSALAIMENANVLAR | | 2606.367 | y | 15 | 3 | 869.8 | 1569.8 | 0.002 |
| CVLKIGEHTPSALAIMENANVLAR | | 2606.367 | y | 14 | 3 | 869.8 | 1472.8 | 0.003 |
| CVLKIGEHTPSALAIMENANVLAR | | 2606.367 | y | 13 | 3 | 869.8 | 1385.8 | 0.006 |
| CVLKIGEHTPSALAIMENANVLAR | | 2606.367 | y | 9 | 3 | 869.8 | 1017.5 | 0.024 |
| IGEHTPSALAIMENANVLAR | | 2106.089 | b | 2 | 3 | 703 | 171.1 | 0.150 |
| IGEHTPSALAIMENANVLAR | | 2106.089 | b | 14 | 3 | 703 | 1464.7 | 0.029 |
| IGEHTPSALAIMENANVLAR | | 2106.089 | b | 18 | 3 | 703 | 1861.9 | 0.001 |
| IGEHTPSALAIMENANVLAR | | 2106.089 | b | 19 | 3 | 703 | 1933 | 0.000 |

Figure 5

| | | | | | | | |
|---|---|---|---|---|---|---|---|
| IGEHTPSALAIMENANVLAR | 2106.089 | y | 15 | 3 | 703 | 1569.8 | 0.016 |
| IGEHTPSALAIMENANVLAR | 2106.089 | y | 14 | 3 | 703 | 1472.8 | 0.020 |
| IGEHTPSALAIMENANVLAR | 2106.089 | y | 8 | 3 | 703 | 886.5 | 0.170 |
| IGEHTPSALAIMENANVLAR | 2106.089 | y | 3 | 3 | 703 | 359.2 | 0.214 |
| IGEHTPSALAIMENANVLAR | 2106.089 | b | 2 | 2 | 1054.1 | 171.1 | 0.080 |
| IGEHTPSALAIMENANVLAR | 2106.089 | b | 3 | 2 | 1054.1 | 300.2 | 0.025 |
| IGEHTPSALAIMENANVLAR | 2106.089 | b | 6 | 2 | 1054.1 | 635.3 | 0.076 |
| IGEHTPSALAIMENANVLAR | 2106.089 | b | 15 | 2 | 1054.1 | 1535.8 | 0.009 |
| IGEHTPSALAIMENANVLAR | 2106.089 | y | 15 | 2 | 1054.1 | 1569.8 | 0.008 |
| IGEHTPSALAIMENANVLAR | 2106.089 | y | 11 | 2 | 1054.1 | 1201.6 | 0.080 |
| IGEHTPSALAIMENANVLAR | 2106.089 | y | 10 | 2 | 1054.1 | 1130.6 | 0.084 |
| IGEHTPSALAIMENANVLAR | 2106.089 | y | 5 | 2 | 1054.1 | 572.4 | 0.102 |
| IGEHTPSALAIMENANVLARYASICQQNGIVPIVEPEILPDGDHDLK | 5107.575 | b | 2 | 5 | 1022.5 | 171.1 | 0.002 |
| IGEHTPSALAIMENANVLARYASICQQNGIVPIVEPEILPDGDHDLK | 5107.575 | b | 9 | 5 | 1022.5 | 906.5 | 0.004 |
| IGEHTPSALAIMENANVLARYASICQQNGIVPIVEPEILPDGDHDLK | 5107.575 | y | 14 | 5 | 1022.5 | 1576.8 | 0.000 |
| IGEHTPSALAIMENANVLARYASICQQNGIVPIVEPEILPDGDHDLK | 5107.575 | y | 12 | 5 | 1022.5 | 1348.7 | 0.002 |
| IGEHTPSALAIMENANVLARYASICQQNGIVPIVEPEILPDGDHDLK | 5107.575 | y | 11 | 5 | 1022.5 | 1251.6 | 0.001 |
| YASICQQNGIVPIVEPEILPDGDHDLK | 3019.497 | b | 2 | 3 | 1007.5 | 235.1 | 0.051 |
| YASICQQNGIVPIVEPEILPDGDHDLK | 3019.497 | b | 15 | 3 | 1007.5 | 1672.8 | 0.000 |
| YASICQQNGIVPIVEPEILPDGDHDLK | 3019.497 | b | 23 | 3 | 1007.5 | 2509.2 | 0.000 |
| YASICQQNGIVPIVEPEILPDGDHDLK | 3019.497 | b | 25 | 3 | 1007.5 | 2761.3 | 0.000 |
| YASICQQNGIVPIVEPEILPDGDHDLK | 3019.497 | y | 13 | 3 | 1007.5 | 1477.7 | 0.007 |
| YASICQQNGIVPIVEPEILPDGDHDLK | 3019.497 | y | 12 | 3 | 1007.5 | 1348.7 | 0.023 |
| YASICQQNGIVPIVEPEILPDGDHDLK | 3019.497 | y | 10 | 3 | 1007.5 | 1122.6 | 0.038 |
| YASICQQNGIVPIVEPEILPDGDHDLK | 3019.497 | y | 4 | 3 | 1007.5 | 512.3 | 0.032 |

SEQUENCE LISTING

<160> NUMBER OF SEQ ID NOS: 32

<210> SEQ ID NO 1
<211> LENGTH: 8

```
<212> TYPE: PRT
<213> ORGANISM: UNKNOWN
<220> FEATURE:
<223> OTHER INFORMATION: transitions generated for the protein
      Fructose-Bisphosphate

<400> SEQUENCE: 1

Glu Leu Ser Asp Ile Ala His Arg
1               5

<210> SEQ ID NO 2
<211> LENGTH: 12
<212> TYPE: PRT
<213> ORGANISM: UNKNOWN
<220> FEATURE:
<223> OTHER INFORMATION: transitions generated for the protein
      Fructose-Bisphosphate

<400> SEQUENCE: 2

Pro His Ser His Pro Ala Leu Thr Pro Glu Gln Lys
1               5                   10

<210> SEQ ID NO 3
<211> LENGTH: 6
<212> TYPE: PRT
<213> ORGANISM: UNKNOWN
<220> FEATURE:
<223> OTHER INFORMATION: transitions generated for the protein
      Fructose-Bisphosphate

<400> SEQUENCE: 3

Ile Val Ala Pro Gly Lys
1               5

<210> SEQ ID NO 4
<211> LENGTH: 20
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 4

Ile Val Ala Pro Gly Lys Gly Ile Leu Ala Ala Asp Glu Ser Thr Gly
1               5                   10                  15

Ser Ile Ala Lys
            20

<210> SEQ ID NO 5
<211> LENGTH: 14
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 5

Gly Ile Leu Ala Ala Asp Glu Ser Thr Gly Ser Ile Ala Lys
1               5                   10

<210> SEQ ID NO 6
<211> LENGTH: 15
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 6
```

```
Gly Ile Leu Ala Ala Asp Glu Ser Thr Gly Ser Ile Ala Lys Arg
1               5                   10                  15

<210> SEQ ID NO 7
<211> LENGTH: 14
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 7

Arg Leu Gln Ser Ile Gly Thr Glu Asn Thr Glu Glu Asn Arg
1               5                   10

<210> SEQ ID NO 8
<211> LENGTH: 13
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 8

Leu Gln Ser Ile Gly Thr Glu Asn Thr Glu Glu Asn Arg
1               5                   10

<210> SEQ ID NO 9
<211> LENGTH: 14
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 9

Leu Gln Ser Ile Gly Thr Glu Asn Thr Glu Glu Asn Arg Arg
1               5                   10

<210> SEQ ID NO 10
<211> LENGTH: 3
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 10

Phe Tyr Arg
1

<210> SEQ ID NO 11
<211> LENGTH: 12
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 11

Phe Tyr Arg Gln Leu Leu Leu Thr Ala Asp Asp Arg
1               5                   10

<210> SEQ ID NO 12
<211> LENGTH: 9
<212> TYPE: PRT
<213> ORGANISM: UNKNOWN
<220> FEATURE:
```

-continued

<223> OTHER INFORMATION: transition generated for the protein
      Fructose-Bisphosphate

<400> SEQUENCE: 12

Gln Leu Leu Leu Thr Ala Asp Asp Arg
1               5

<210> SEQ ID NO 13
<211> LENGTH: 27
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 13

Gln Leu Leu Leu Thr Ala Asp Asp Arg Val Asn Pro Cys Ile Gly Gly
1               5                   10                  15

Val Ile Leu Phe His Glu Thr Leu Tyr Gln Lys
            20                  25

<210> SEQ ID NO 14
<211> LENGTH: 18
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 14

Val Asn Pro Cys Ile Gly Gly Val Ile Leu Phe His Glu Thr Leu Tyr
1               5                   10                  15

Gln Lys

<210> SEQ ID NO 15
<211> LENGTH: 30
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 15

Val Asn Pro Cys Ile Gly Gly Val Ile Leu Phe His Glu Thr Leu Tyr
1               5                   10                  15

Gln Lys Ala Asp Asp Gly Arg Pro Phe Pro Gln Val Ile Lys
            20                  25                  30

<210> SEQ ID NO 16
<211> LENGTH: 12
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 16

Ala Asp Asp Gly Arg Pro Phe Pro Gln Val Ile Lys
1               5                   10

<210> SEQ ID NO 17
<211> LENGTH: 14
<212> TYPE: PRT
<213> ORGANISM: UNKNOWN
<220> FEATURE:
<223> OTHER INFORMATION: transitions generated for the protein
      Fructose-Bisphosphate

```
<400> SEQUENCE: 17

Ala Asp Asp Gly Arg Pro Phe Pro Gln Val Ile Lys Ser Lys
1               5                   10

<210> SEQ ID NO 18
<211> LENGTH: 9
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 18

Ser Lys Gly Gly Val Val Gly Ile Lys
1               5

<210> SEQ ID NO 19
<211> LENGTH: 7
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 19

Gly Gly Val Val Gly Ile Lys
1               5

<210> SEQ ID NO 20
<211> LENGTH: 10
<212> TYPE: PRT
<213> ORGANISM: UNKNOWN
<220> FEATURE:
<223> OTHER INFORMATION: transitions generated for the protein
      Fructose-Bisphosphate

<400> SEQUENCE: 20

Gly Gly Val Val Gly Ile Lys Val Asp Lys
1               5                   10

<210> SEQ ID NO 21
<211> LENGTH: 26
<212> TYPE: PRT
<213> ORGANISM: UNKNOWN
<220> FEATURE:
<223> OTHER INFORMATION: transitions generated for the protein
      Fructose-Bisphosphate

<400> SEQUENCE: 21

Val Asp Lys Gly Val Val Pro Leu Ala Gly Thr Asn Gly Glu Thr Thr
1               5                   10                  15

Thr Gln Gly Leu Asp Gly Leu Ser Glu Arg
            20                  25

<210> SEQ ID NO 22
<211> LENGTH: 23
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 22

Gly Val Val Pro Leu Ala Gly Thr Asn Gly Glu Thr Thr Thr Gln Gly
1               5                   10                  15

Leu Asp Gly Leu Ser Glu Arg
```

```
<210> SEQ ID NO 23
<211> LENGTH: 28
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 23

Gly Val Val Pro Leu Ala Gly Thr Asn Gly Glu Thr Thr Thr Gln Gly
1               5                   10                  15

Leu Asp Gly Leu Ser Glu Arg Cys Ala Gln Tyr Lys
            20                  25

<210> SEQ ID NO 24
<211> LENGTH: 5
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 24

Cys Ala Gln Tyr Lys
1               5

<210> SEQ ID NO 25
<211> LENGTH: 8
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 25

Lys Asp Gly Ala Asp Phe Ala Lys
1               5

<210> SEQ ID NO 26
<211> LENGTH: 7
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 26

Asp Gly Ala Asp Phe Ala Lys
1               5

<210> SEQ ID NO 27
<211> LENGTH: 9
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 27

Asp Gly Ala Asp Phe Ala Lys Trp Arg
1               5

<210> SEQ ID NO 28
<211> LENGTH: 4
<212> TYPE: PRT
<213> ORGANISM: UNKNOWN
```

```
<220> FEATURE:
<223> OTHER INFORMATION: transition generated for the protein
      Fructose-Bisphosphate

<400> SEQUENCE: 28

Cys Val Leu Lys
1

<210> SEQ ID NO 29
<211> LENGTH: 24
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 29

Cys Val Leu Lys Ile Gly Glu His Thr Pro Ser Ala Leu Ala Ile Met
1               5                   10                  15

Glu Asn Ala Asn Val Leu Ala Arg
            20

<210> SEQ ID NO 30
<211> LENGTH: 20
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 30

Ile Gly Glu His Thr Pro Ser Ala Leu Ala Ile Met Glu Asn Ala Asn
1               5                   10                  15

Val Leu Ala Arg
            20

<210> SEQ ID NO 31
<211> LENGTH: 47
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 31

Ile Gly Glu His Thr Pro Ser Ala Leu Ala Ile Met Glu Asn Ala Asn
1               5                   10                  15

Val Leu Ala Arg Tyr Ala Ser Ile Cys Gln Gln Asn Gly Ile Val Pro
            20                  25                  30

Ile Val Glu Pro Glu Ile Leu Pro Asp Gly Asp His Asp Leu Lys
        35                  40                  45

<210> SEQ ID NO 32
<211> LENGTH: 27
<212> TYPE: PRT
<213> ORGANISM: UNKNOWN
<220> FEATURE:
<223> OTHER INFORMATION: transition generated for the protein
      Fructose-Bisphosphate

<400> SEQUENCE: 32

Tyr Ala Ser Ile Cys Gln Gln Asn Gly Ile Val Pro Ile Val Glu Pro
1               5                   10                  15

Glu Ile Leu Pro Asp Gly Asp His Asp Leu Lys
            20                  25
```

METHODS AND SYSTEMS FOR SEQUENCE-BASED DESIGN OF MULTIPLE REACTION MONITORING TRANSITIONS AND EXPERIMENTS

This application claims the benefit of priority of U.S. Provisional Applications 60/807,100 filed Jul. 12, 2006 and 60/932,730 filed Jun. 2, 2007 both of which are incorporated by reference in their entirety.

FIELD

The present teachings encompass computational methods and systems, implementable in software, for the design of proteomic experiments.

BACKGROUND

Global proteomics approaches have dominated the field of mass spectrometry for the study of proteins and biomarkers. Increasingly, more targeted approaches are being used for understanding biological problems. In the past year or two, a trend towards hypothesis-driven discovery has emerged. Hypothesis-driven approaches can be beneficial in that they typically focus on collecting data that will answer a specific biological question and thus reduce resources used to collect what is often extraneous data. Although more focused, hypothesis-driven approaches are still limited by the number of mass spectrometry scans that can be performed in a single experiment. One approach to maximize the utility of collected data is the Selective Reaction Monitoring ("SRM") experiment. In a SRM experiment on a triple-quadrupole mass spectrometer, the first quadrupole (Q1) is set to pass ions only of a specified m/z (precursor ions) of an expected chemical species in the sample. The second quadrupole (i.e. Q2 or the collision cell) is used to fragment the ions passing through Q1. The third quadrupole (Q3) is set to pass to the detector only ions of a specified m/z (fragment ions) corresponding to an expected fragmentation product of the expected chemical species. When numerous SRM experiments are run, as is typically the case, the process is called Multiple Reaction Monitoring ("MRM".) MRM scans have excellent specificity because very few chemical species will share the combination of precursor m/z and fragment m/z values specified. The pair of m/z values is termed the "MRM transition" or alternately, the parent-daughter ion transition pair "PDITP" being monitored. One example of an MRM workflow is the MIDAS workflow (PDITP Initiated Detection And Sequencing), where signal in a PDITP channel will trigger the acquisition of a full scan MS/MS on the parent ion to confirm the peptide identity. The present teachings can enable this, and other MRM-related workflows, with greater efficiency, specificity and sensitivity.

In the MIDAS workflow, a software script can be used to determine Q1 and Q3 masses based on a protein sequence. Basic rules can be used to determine the masses. Generally, no prioritization of PDITPs is performed. Large lists of PDITPs are built which must then be manually curated by user. Many hypotheses can be tested using PDITP transitions but as the proteins get larger or if more proteins need to be tested, the maximum number of PDITPs for the acquisition method can be quickly exceeded. Thus, the script is limited to processing a few proteins at a single time. Because of the simple logic in such scripts, and no effective way of screening for the most likely peptides to be observed or the most intense PDITPs to monitor, the list of PDITP quickly expands. Only up to ~150 PDITPs can be monitored in a single time period, therefore PDITP transitions to only a few proteins can be built into a single acquisition method. With the number of candidate biomarkers coming out of the biomarker discovery platforms, there is a great need to have a more efficient method of developing mass spectrometry methods for validating which markers are the most promising (the most diagnostic or prognostic). With the present teachings, more efficient PDITP driven discovery methods requiring minimal user curation (such as PDITP driven MS/MS experiments) can be designed.

DESCRIPTION OF FIGURES

FIG. 5 lists 293 transitions generated for the protein Fructose-Bisphosphate according to various embodiments, and their respective probabilities of detection.

DESCRIPTION

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Computer Implemented System

Figure 1:
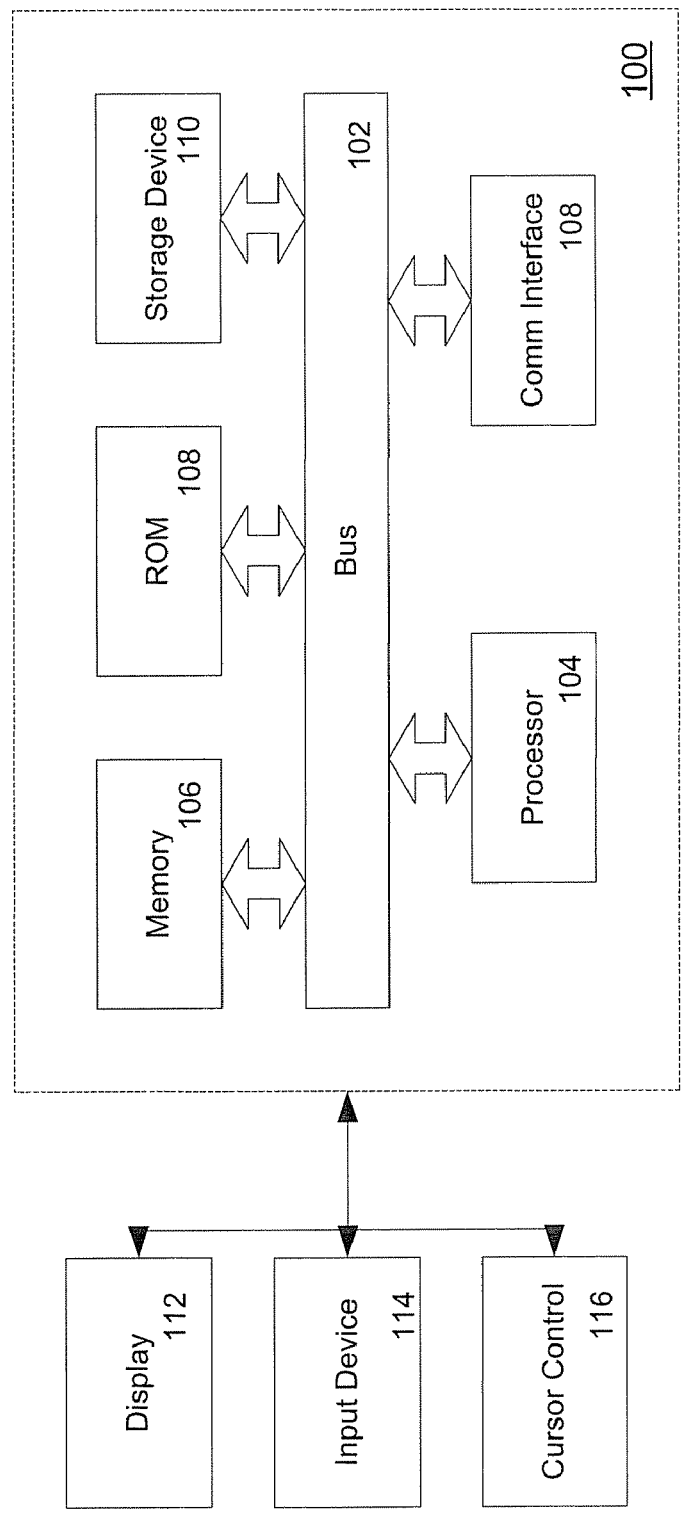
FIG. 1 is a block diagram that illustrates a computer system, upon which embodiments of the present teachings may be implemented.

FIG. 1 is a block diagram that illustrates a computer system 100, upon which embodiments of the invention may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102, and instructions embodying aspects of the present teachings to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user.

An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

A computer system 100 performs aspects of the present teachings such as PDITP transition prediction and prioritization. Consistent with certain implementations of the invention, PDITP transition pairs and prioritization are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the invention. Thus implementations of the invention are not limited to any specific combination of hardware circuitry and software.

The term "computer-readable medium" as used herein refers to any media that participates in providing instructions to processor 104 for execution. Such a medium may take many forms, including but not limited to, non-volatile media or volatile media. Such a medium does not include transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

The descriptions of implementations of the present teachings herein have been presented for purposes of illustration and description. It is not exhaustive and does not limit the invention to the precise forms disclosed. Modifications and variations are possible in light of the above teachings or may be acquired from practicing of the invention. Additionally, the described implementation includes software but the present invention may be implemented as a combination of hardware and software or in hardware alone. The invention may be implemented with both object-oriented and non-object-oriented programming systems.

Description

The term "parent-daughter ion transition monitoring" or "PDITM" refers to, for example, a measurement using mass spectrometry whereby the transmitted mass-to-charge (m/z) range of a first mass separator (often referred to as the first dimension of mass spectrometry) is selected to transmit a molecular ion (often referred to as "the parent ion" or "the precursor ion") to an ion fragmentor (e.g., a collision cell, photodissociation region, etc.) to produce fragment ions (often referred to as "daughter ions") and the transmitted m/z range of a second mass separator (often referred to as the second dimension of mass spectrometry) is selected to transmit one or more daughter ions to a detector which measures the daughter ion signal. The combination of parent ion and daughter ion masses monitored can be referred to as the "parent-daughter ion transition" monitored. The daughter ion signal at the detector for a given parent ion-daughter ion combination monitored can be referred to as the "Parent-Daughter Ion Transition Pair ("PDITP") signal".

The term "multiple reaction monitoring" or "MRM" scan or MRM experiment refers to an embodiment of PDITM. It is also sometimes referred to as "selective reaction monitoring." In various embodiments, a PDITM can be performed, for example, by parking the first mass separator on parent ion m/z of interest to transmit parent ions and scanning with a second mass separator over a m/z range including the m/z value of the daughter ion of interest and, e.g., extracting an ion intensity profile from the spectra. Typically, when using a triple quadrupole mass spectrometer to perform MRM scans, the first quadrupole (Q1) is parked on the parent ion m/z, and therefore is transmitting only the parent ion of interest. This ion is then fragmented in the collision cell at a pre-determined collision energy (or a collision energy determined on the fly). The fragment ions are transmitted through the collision cell to the third quadrupole (Q3). Q3 is set to transmit only the predetermined fragment ion of interest and this ion then hits the detector. Generally, an MRM scan has one of the highest duty cycle/sensitivity of all mass spectrometry scans. A tandem mass spectrometer (MS/MS) instrument or, more generally, a multidimensional mass spectrometer (MSn) instrument, can be used to perform PDITM. A wide variety of mass analyzer systems can be used in conjunction with the present teachings. Suitable mass analyzer systems include two mass separators with an ion fragmentor disposed in the ion flight path between the two mass separators. Examples of suitable mass separators include, but are not limited to, quadrupoles, RF muiltipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, or combinations thereof. Examples of suitable mass spectrometry systems for the mass analyzer include, but are not limited to, those which comprise a triple quadrupole, a quadrupole-linear ion trap, a quadrupole TOF systems, and TOF-TOF systems. Suitable ion sources for the mass spectrometry systems include, but are not limited to, an electrospray ionization (ESI), matrix-assisted laser desorption ionization (MALDI), atmospheric pressure chemical ionization (APCI), and atmospheric pressure photoionization (APPI) sources. For example, ESI ion sources can serve as a means for introducing an ionized sample that originates from a LC column into a mass separator apparatus. One of several desirable features of ESI is that fractions from the chromatography column can proceed directly from the column to the ESI ion source.

Figure 2:
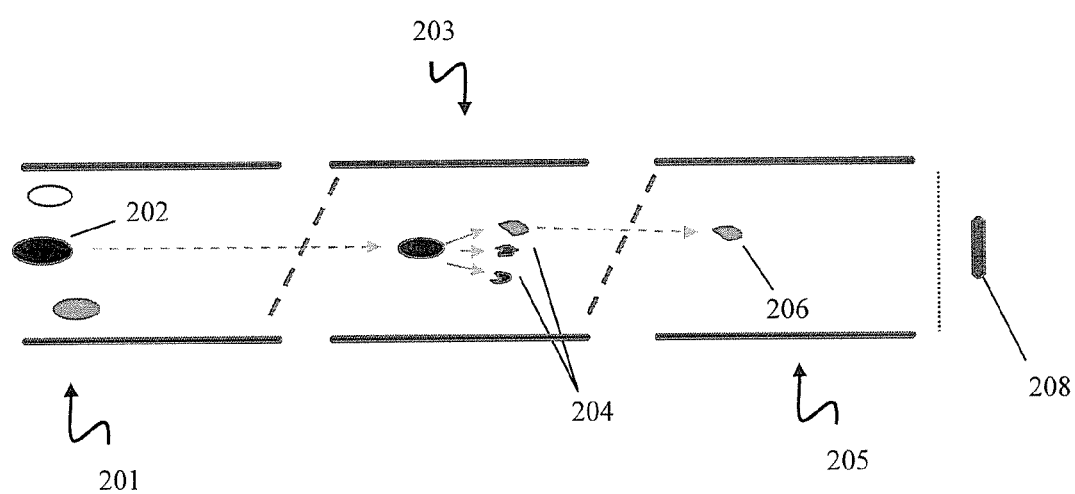
FIG. 2 is a simplified schematic diagram of a mass spectrometer implementing a MRM-type experiment.

Referring to FIG. 2, a MRM scan can be conducted, for example, by setting the first mass separator 201 (in the instrument used the first mass separator is a quadrupole) to transmit the signature peptide of interest (i.e., the parent ion 202, e.g., by setting the first mass separator to transmit ions in a mass window about 3 mass units wide substantially centered on the mass of a signature peptide). In various embodiments, the collision energy can be selected to facilitate producing the selected diagnostic charged fragment of this peptide (the selected diagnostic daughter ion) in the ion fragmentor (here the ion fragmentor comprises a collision gas for conducting CID and a quadrupole 203, to facilitate, e.g., collecting ion fragments 204 and fragment ion transmittal); and the second mass separator 205 (in the instrument used the second mass separator is a quadrupole configurable as a linear ion trap) is set to transmit the diagnostic daughter ion (or ions) 206 of interest (e.g., by setting the second mass separator to transmit ions in a mass window about 1 mass unit wide substantially centered on the mass of a diagnostic daughter ion) to a detector 208 to generate an ion signal for the diagnostic daughter ion (or ions) transmitted.

The term "peptide of interest" or "POI" refers to a peptide that is the focal point of an experiment. The presence, or elevated/suppressed levels, of a POI may be indicative of a certain disease state. Typically, in such a case, the POI is referred to as a biomarker. Biomarkers are typically defined as any molecular species found to provide correlation to a particular phenotype or perturbation of a biological system. Detecting biomarkers specific to a disease can aid in the identification, diagnosis, and treatment of affected individuals and people who may be at risk but do not yet exhibit symptoms. Co-variant analysis of multiple biomarkers or patterns usually results in higher correlation confidence.

In various embodiments, input data is one or more protein or peptide sequences. These sequences can come from a variety of sources such as protein sequence databases or gene sequence databases. The choice of the proteins to be investigated can also come from many sources, such as a previous protein identification experiment, or a biomarker discovery experiment (proteomic or genomic). The protein sequences may also be accompanied with prior experimental data such as abundance measurements (either absolute or relative), peptide identifications, or mass spectral data from which the proteins were identified. The user can also specify as input the goal of the experiment, such as protein discovery, post-translational modification "PTM" discovery, ID validation etc. and other variables as appropriate and as will be elucidated further in this document. For samples already prepared for mass spec, the user can also supply sample preparation information such as digestion enzyme used, cysteine modification, protein source (solution digestion or gel based workflow), and other information that might affect the integrity of the peptides generated.

PDITP Candidate Selection for MRM Scans

One function of certain embodiments of the present teachings is to score and rank PDITPs for various proteins. In various embodiments PDITP candidates can be generated by examining the protein under study and first determining where peptides are likely to form. This can be accomplished for example in the instance of a tryptic digestion where the enzyme trypsin cuts a protein at specific sites. This process can be used to generate the parent ion of the PDITP. In some cases provisions for missed cleavages or other observed modifications can be incorporated in predicting the peptides. Theoretical daughter ions can then be generated by fracturing the peptides at various points along their peptide backbone. If all ion combinations of parent and daughter ions are considered, and particularly if missed-cleavages, port-translational modifications and the like are taken into account, the number of theoretically possible PDITPs for even a single protein can be large. However, many PDITPs can be eliminated from consideration based on simple checks. For example, a filtering step can be used that may consist of selecting a promising subset of PDITPs worthy of further consideration. This can be valuable when the scoring of PDTIPs in next stage is computationally expensive. Quick selection by pre-filtering may be based on a simple scoring scheme based on a subset of the factors used for scoring candidates in subsequent stages. In various embodiments, the list of peptides to be injected into the mass spectrometer may already be known.

PDITP Scoring

In various embodiments, the selected PDITP candidates are each scored and the ion pair and its score is stored with its corresponding peptide and protein. Various embodiments score PDITP candidates and rank the candidates due to their scores. This can be beneficial as compared to simple filtering because in filtering, the order of application of the filters is important. For example, an early filter may remove a candidate from consideration even though it may pass all other tests and actually be superior to many other candidates retained via the filtering process. The scoring of the PDITPs can consider the ease of detecting the target protein via the PDITP, as well as the scientific value of the detection in the context of the user's experimental goal. For example, factors pertaining to the use of a PDITP address issues including, but not limited to the following.

The detectability of a PDITP can be assessed based on variables that relate to the observation of peptides from a protein (via enzymatic digestion and MS analysis), and variables that relate to the observation of fragment ions from a peptide (via fragmentation and MS/MS analysis). These variables can include: charge state, molecular weight, detection in previous MS/MS data (e.g. based on other biomarker discovery software packages, such as ProteinPilot or MarkerView both from Applied Biosystems, Foster City, Calif., USA), enzyme digestion specificity/efficiency, and MS ionization efficiency. Also, in cases where the mass spectrometer is fed from a chromatographic system, retention time prediction can be used to help parse PDITPs into multiple time windows, or dynamically created overlapping PDITP windows. In addition, modification sites on a peptide, the consensus sequence for desired post-translational modification, sites for unwanted modification (ie. oxidation of Methionine residues will reduce the detection of unmodified peptide), and the intensity of Q3 fragment ion mass can also be considered.

For the peptides being considered, various embodiments can determine the tendency of a given PDITP to produce a strong signal. For example, rules and probabilities known in the literature can be used to determine the probability of a certain type of fragmentation occurring. This can be useful since a PDITP with a strong signal, but that only occurs occasionally due to imperfect fragmentation, may not be as favorable as a PDITP that generates a weaker signal but will occur more reliably. In various embodiments fragmentation patterns can be predicted and peptide sequence ions expected to have the highest signal can be prioritized and probabilities of observing specific fragments can be assessed and rules developed based specifically on fragmentation in a collision cell or previously published rules could be incorporated (Kapp et al (2003) Anal Chem 75(22), 6251.) One skilled in the art can make use of a variety of published rules and their probabilities. Other rules and probabilities may be experimentally or theoretically determined over time.

The utility of detecting a PDITP can be quantified to indicate how well that PDITP will address the goals specified by the user at the start of the experiment. In various embodiments, a probability or weighting based on utility can then be added into the joint consideration of multiple factors. For example, if detecting differential expression between isoforms is a goal of the experiments, one measure of utility for a PDITP is the chance that the parent peptide provides an expression measurement specific to a particular isoform. Peptides known from a previous experiment to be shared by multiple detected isoforms in the sample would have a low value for this metric. If protein ID validation is the goal, shared peptides can be considered as useful or nearly as useful as isoform-distinct peptides. If detecting peptide modifications is a goal, prior knowledge about likely modifications can influence the measure of utility. For example, if phosphorylation is requested on Ser/Thr/Tyr and information is known about the consensus sequence expected or the kinase associated, this site will have a higher probability or weighting but other sites will be considered as well with lower probability or weighting. In various MRM experiments, biomarker verification normalization peptides are often included in the sample for precise quantitative measurements. When normalization peptides are included, a measurement of the normalization peptides is generally required, and thus the measure so some the utility of having at least a minimal number of them can be reflected in the utility metric.

Additional factors relating to the utility of a PDITP may include uniqueness of peptide (relative to database or other protein isoforms) and specificity of the PDITP (i.e. specificity of the Q1/Q3 pair). Specificity can be a particularly vexatious problem. For MRM experiments, it is often important that the chosen PDITP only correspond to one protein. While protein homology searching can be performed between the input proteins to determine if two or more proteins can produce the same parent and daughter ions, absence of a match may not be dispositive that absolute specificity exists. This is due to the fact that the mass spectrometer measures masses and not sequences. Therefore, two peptides or fragments may share the same mass value yet have a different arrangement of the constituent amino acids, or they may even have different amino acid sequences altogether. In some instances, modifications to an amino acid may lead to a daughter ion having the same mass as that of another peptide or fragment yet possess a different sequence. In the above cases, the non-specificity can lead to a false positive detection and in cases where ions are quantitated, can lead to a falsely high reading for the protein. Thus various embodiments can compute the likely modifications for theoretical daughter ions, and compare the masses to a given PDITP.

A MRM experiment is generally only useful in quantifying a protein or post-translational modification if it can detect the species sought with high specificity. Specificity is defined as the degree to which a specific peptide PDITP can uniquely detect and quantify the specific peptide of interest, with minimal (and ideally no) interference from another co-eluting peptide. To interfere, the other species must produce signal in both the Q1 and Q3 m/z of the peptide of interest. Interference can be the result of 1) a peptide with the same sequence as the POI or 2) a peptide with a totally different sequence that happens to produce the same Q1 and Q3. The specificity of a PDITP can be measured experimentally or calculated in silico.

A POI might suffer from quantitative interference if it possesses the exact (nonunique) sequence of a peptide from another protein. Thus, peptide uniqueness can be used as a measure in determining the propriety of using a particular PDITP. If it is known that the interfering peptide is from a protein that is not expressed under the biological condition being monitored, then it can be used in the assay. Methods of protein homology detection, otherwise known as protein sequence alignment are well known to those of skill in the art. For examples based on Hidden-Markov Models see Bioinformatics, 2005 Apr. 1; 21(7):951-60, Epub 2004 Nov. 5, which also discusses popular methods such as BLAST, PSI-BLAST, HMMER and the profile-profile comparison tools PROF_SIM and COMPASS. Several of these methods report similarity scores that can be useful in determining the uniqueness of a peptide with regard to another. Where there is homology between the POI and the interfering peptide, and the degree of homology is high, the chances of finding a unique PDITP are low, however, if only small regions are homologous, chances of finding a PDITP are generally higher. One skilled in the art will appreciate that the similarity scores can be converted to probabilities and used in a multi-factor scoring analysis as discussed herein.

Specificity can also be determined by identifying whether or not there is a peptide that shares the Q1 and Q3 m/z of the POI, even though the sequence is not the same. In these cases, the specific PDITP should be avoided, however, the problem may be overcome by considering additional PDITPs. For example, if PDITP-X can be found in both Peptide-A and Peptide-B, PDITP-X is likely not a suitable candidate for use in MRM on its own. Similarly, if PDITP-Y can be found in both Peptide-A and Peptide-B, PDITP-Y will likely not be suitable for MRM on its own, however, performing an MRM scan and looking for signals from both PDITP-X and PDITP-Y will permit disambiguation of Peptides—A, B, and C.

Various embodiments contemplate the use of the same precursor ion but use of two or more daughter ions for POI identification. For example if two daughter ions of the same precursor ion are used, the resulting transition set can be referred to as a Parent Daughter Ion Transition Triple ("PDITT"). In the case of protein identification, such a PDITT can be formed by choosing a precursor ion, and generating its theoretical fragments, and comparing the precursor's theoretical fragment masses to fragment masses contained in a library of alternate fragment masses (the "Library".) The Library can be formed by first finding all alternate peptides with mass-to-charge ratios similar enough to the precursor ion so as to likely be included with the precursor when the precursor ion is selected by Q1 and subsequently determining all theoretical fragments for the alternate peptides. If no unique PDITP can be found after the comparison, the comparison can be continued so as to include an additional daughter ion where the additional daughter ion causes the creation of a triple (parent, daughters and daughter2) that is unique to the protein. In this way the situation where Peptide-1, Peptide-2 and Peptide-3 are all likely to be selected by Q1 and Peptide-1 is from Protein-A, and Peptide-2 is from Protein-B, and Peptide-3 is from Protein-C, and the goal is to positively identify Protein-B and no unique PDITP exists to positively identify Protein-B and Peptide-1 and Peptide-2 have ions with Mass-1 in common, and Peptide-2 and Peptide-3 have ions with Mass-2 in common, an MRM scan that looks for masses associated with Peptide-2 and Mass-1 and Mass-2 can result in positive identification of Protein-B. One skilled in the art will appreciate that this concept can be extended beyond the PDITT to include a set with more than 2 daughter ions. Also, where the present teachings refer to a PDITP, one skilled in the art will appreciate that a parent-daughter ion transition involving two or more daughter ions can also be substituted.

IN various embodiments, experimental determination of specificity can be performed by testing the PDITPs of interest in the biological sample ideally under the sample prep conditions that will be used for the quantitative assay. In an MRM experiment, it is often ideal that the PDITP is a single component, with no interfering species eluting close enough in time (if using liquid chromatography) to interfere with the proper integration of the peak of interest. The advantage of this method is that non-peptidic contaminants will be considered. Specificity of a PDITP for MRM use can be determined by peak shape. For example, the instance where Peptide-A with PDITP-X eluting at a retention time of 25 mins, and Peptide-B with PDITP-Y eluting at a retention time of 20 mins occurs, would not lead to a specificity issue because the different elution times allow each component to be successfully quantified. However, if Peptide-B eluted at 24.5 mins, its peak area would likely blend with the peak area of Peptide-A and quantitation would be difficult. Specificity can be measured by MS/MS analysis of the PDITP peaks. In addition to assessing the peak shape, MS/MS analysis can be performed on the Q1 mass of the PDITP of interest and the resulting fragmentation spectrum can be assessed for the presence of a second interleaved fragment ion pattern that would suggest the presence of an additional component. This can be done by manual inspection or by using an algorithm (such as Paragon™ Algorithm by Applied Biosystems, Foster City, Calif.) that is capable of discerning multiple components in MS/MS spectra. Additional experimental determination can be performed by using databases of previously acquired LCMS/MS. These databases of spectra can be mined for Q1/Q3 pairs that could produce interfering species. Where a peptide PDITP's specificity has been assessed experimentally by an above method, the information can be used in the computation of the utility of the PDITP.

Various embodiments perform in silico prediction of specificity by identifying every peptide from a protein database that could produce a Q1 with a given m/z within a specified m/z tolerance. This can be performed by in silico digestion and computation of charge states that could be observed by electrospray. Then for the population of peptides with within-tolerance Q1 m/z values, theoretical fragmentation patterns can be computed using typical fragmentation rules. Any peptide in this sub-population that also produces a fragment ion of the Q3 m/z of Peptide A is considered a possible interfering species and lowers the specificity of the PDITP used for detecting Peptide-A. Common sample preparation issues (alkylation of cysteine residues, digestion agent used, presence of oxidized methionines, etc.) can be considered in the computations. More refined techniques make use of additional factors to provide a more realistic view of the sample, and not overly penalize specific PDITPs for contaminations that might not be detectable, nor under penalize specific PDITPs because the real contamination was not considered appropriately.

Various embodiments employ methods that perform the in silico digestion and consider peptides that could produce a Q1 with the same Q1 m/z as the POI within the specified m/z tolerance by adding the masses of modifications to the peptide products of the in silico digested proteins. For example, Peptide-A which results from in silico digestion may not have a Q1 m/z matching that of the POI, however, with the addition of a phosphorylation, it might match. Then theoretical fragmentation patterns of Peptide-A can be computed and compared. Modifications can be taken into account at this stage as well.

Various embodiments take into account the dynamic range of protein expression present in all biological samples. If a contamination is present in the sample but not detectable within the dynamic range of the mass spectrometer, then it will not interfere with quantitation of the POI. Knowledge about the dynamic range of the sample can be leveraged and applied as a probabilistic weighting of the contamination of the MRM. Knowledge of dynamic range can be found in the scientific literature or it can come from experimental analysis. For example, if an extensive LCMS/MS characterization of the sample is performed, the kinds of proteins that are detectable in the dynamic range of experiment will be apparent. Peptides from this population of proteins detected with many peptides can be considered the most likely to provide possible contaminants to the proteins of interest. Proteins detected with very few peptides are likely lower abundance and therefore less likely to contribute contaminating peptides. Proteins not detected at all have the lowest probability of producing contaminating peptides. For proteins that have the highest probability of producing contaminant peptides, various embodiment consider more features such as modifications, etc. For example a missed cleavage on a high abundance protein is more likely to produce interference than a true tryptic peptide from a protein that wasn't detected. As another example, a low level phosphorylation on a more abundant protein is more likely to be seen than a frequent modification on a protein that is not detected. Various embodiments identify more probable events and emphasize them in searching out interfering peptides while minimizing the search for interfering peptides that might be due to low probability events. This technique can greatly improve PDITP identification as it biases the search space and computational power towards more likely outcomes.

While various embodiments consider multiple factors serial and thus filter the list of PDITPs, various embodiments also consider the factors jointly by associating each with a probability or weighting and combining these probabilities. For example, one factor for a PDITP is that the peptide must be present in the prepared sample and observed via MS analysis. When trypsin is used as the digest agent there is often also small number of chymotryptic cleavages that can be present in the sample. Tryptic peptides therefore can receive a high probability or weighting, while peptides with a chymotryptic terminus can receive a lower probability or weighting. In various embodiments, the combination of rules used in the generation of the peptides and their PDITPs can lead to a probability or weighting of good detection of each PDITP can be calculated. This can be based on the joint probability or weighting of some or of all the factors that determine the peptide and the PDITP. Various embodiments consider these issues jointly by selecting PDITP transitions on a maximum likelihood basis. In such instances, given the hypothesis that a protein of interest (or PTM of interest, etc.) is present, the joint probability of the PDITP transition being observed and being useful towards the stated goal is calculated.

In various embodiments, the candidate selection and scoring steps are intertwined. For example, branch-and-bound is a general algorithmic method for finding optimal solutions of various optimization problems, especially in discrete and combinatorial optimization. It is an enumeration approach that prunes nonpromising search spaces. Numerous references on the branch-and-bound technique exist, as one skilled in the art will know, as it was first proposed in 1960 and has been well studied since that time. To apply branch-and-bound to MRM experiment design, a tree structure can be designed that can accommodate all of the PDITPs possible for a protein or a set of proteins and each leaf of the tree corresponds to a specific PDITP. A bound function can then be defined so that at any given node in the tree, a bound can be calculated on the best PDITP score possible under that node. A branch of the tree can be eliminated from further consideration once the bound on its root node is such that no PDITP from that branch could rank high enough to enter the list of the top N PDITPs already found. Algorithms such as branch-and-bound can be terminated after a reasonable computation time to yield a set of good transitions that have not yet been proven optimal. One skilled in the art will appreciate that other algorithms can be substituted for the branch and bound algorithm.

Once individual PDITPs have been scored, an aggregate list of PDITPs to be studied in an experiment can be determined. Various embodiments base the final PDITP list on the PDITP scores and the goals of the experiment. Various embodiments form this list in different ways. For example, a simple approach is to select the top N PDITPs. Here, all scored PDITPs can be placed in a simple ranked list, and the top N PDITPs are retained and used in the subsequent experiment. Various other schemes can be employed such as difference the scores for subsequent PDITPs and examining the differences for a point where the differences increase significantly. This point can then become a cutoff in determining which PDITPs remain on the list to be reported to the user. In various embodiments, PDITPs can be ranked separately for each protein, and a certain number of PDITPs per protein can be chosen by any method that might be used on the complete list of PDITPs from all proteins. Various embodiments take chromatographic information into account in the determination of the optimal number of PDITP transitions to be used in the final method (LC peak width, sensitivity required defines dwell time, etc.). Various embodiments select PDITP to achieve a certain probability of observing at least one of them. Also, entropy-based metrics can be considered for deciding which additional transitions have the most impact on improving the detection of features of interest.

In some embodiments, a metric is defined that reflects the value of a set of PDITP transitions in the context of a particular experimental goal. The present teachings span the construction, calculation and optimization of such a metric. Example metrics to optimize include, the number of proteins predicted to be detected with at least a specified level of confidence, and the expected value of a reward function. The reward function could be a sum of weights assigned to each sample feature (protein or peptide) detected. The expected value of the reward function could then be:

Sum {weight_i*probability_of_detection_i}, where weight_is the weight or value of the i-th sample feature of interest and probability_of_detection_i is the probability of detecting the i-th sample feature.

The present teachings can perform a multivariate optimization to select the set of PDITPs that has the highest value for the metric defined. Multivariate methods that can be used for the optimization include but are not limited to Simulated Annealing (SA), Tabu Search (TS), Genetic Algorithm (GA), Genetic Programming (GP), Memetic Algorithm (MA), Neural Networks (NN), Ant colony optimization (ACO).

If more information is required in a single run, time information (such as set time periods or retention times with time windows) can be used in the acquisition method to increase the number of PDITPs to be used. Chromatographic retention time prediction can be used to put possible PDITPs in the right chromatographic time periods. Time information can be used to maximize the number of PDITPs per acquisition method by including the probability of a peptide eluting a particular time in the overall PDITP probability. In this way, the score of a PDITP is a function of retention time.

Instrument conditions can be calculated for each PDITP in the final method, important conditions such as collision energy can be used. Other parameters that could affect ionization or transmission of the ion could also be adjusted.

Figure 3:
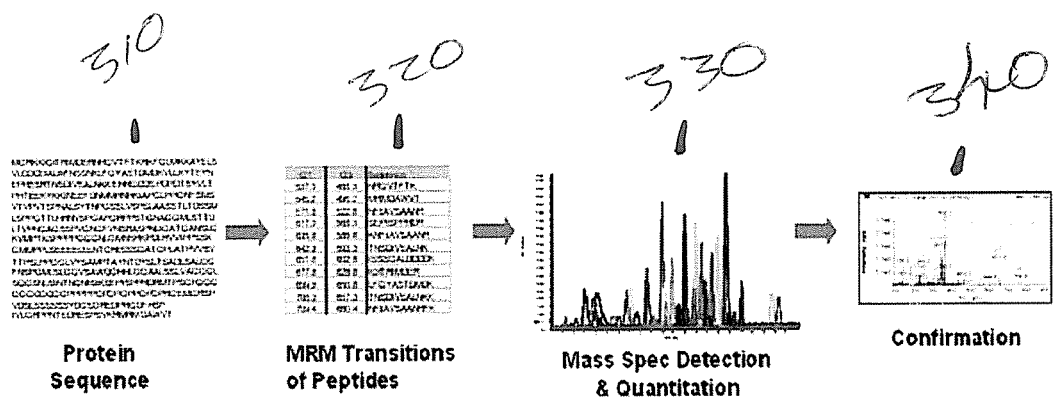
FIG. 3 illustrates a MRM scan-triggered data acquisition workflow for discovery and validation. In this workflow, the PDITPs are design based on a known protein sequence. By applying a set of rules, the Q1 and Q3 masses of the PDITPs can be predicted from the protein sequence and used to detect the hypothesized peptide in a complex mixture with high specificity and sensitivity. Once the PDITP signal is detected, the instrument switches to ion trap mode and collects a full scan MS/MS spectrum to confirm the identity of the detected peptide or component.

Once a method has been created, it can be run on an instrument capable of performing a MRM-like scan (such as a triple quadrupole mass spectrometer or a Q TRAP system). Various embodiments consider workflows as illustrated in FIG. 3 where a POI (310) has applied to it the present teachings in order to produce a set of PDITPs (320), a mass spectrometer scan for the selected PDITPS (330) and when a PDITP signal is observed, a full scan MS/MS can be triggered to confirm that the identity of the peptide eluting and that PDITP signal is indeed the predicted peptide (340). This confirmation can be done by fragment ion matching to the hypothesized peptide.

Figure 4:
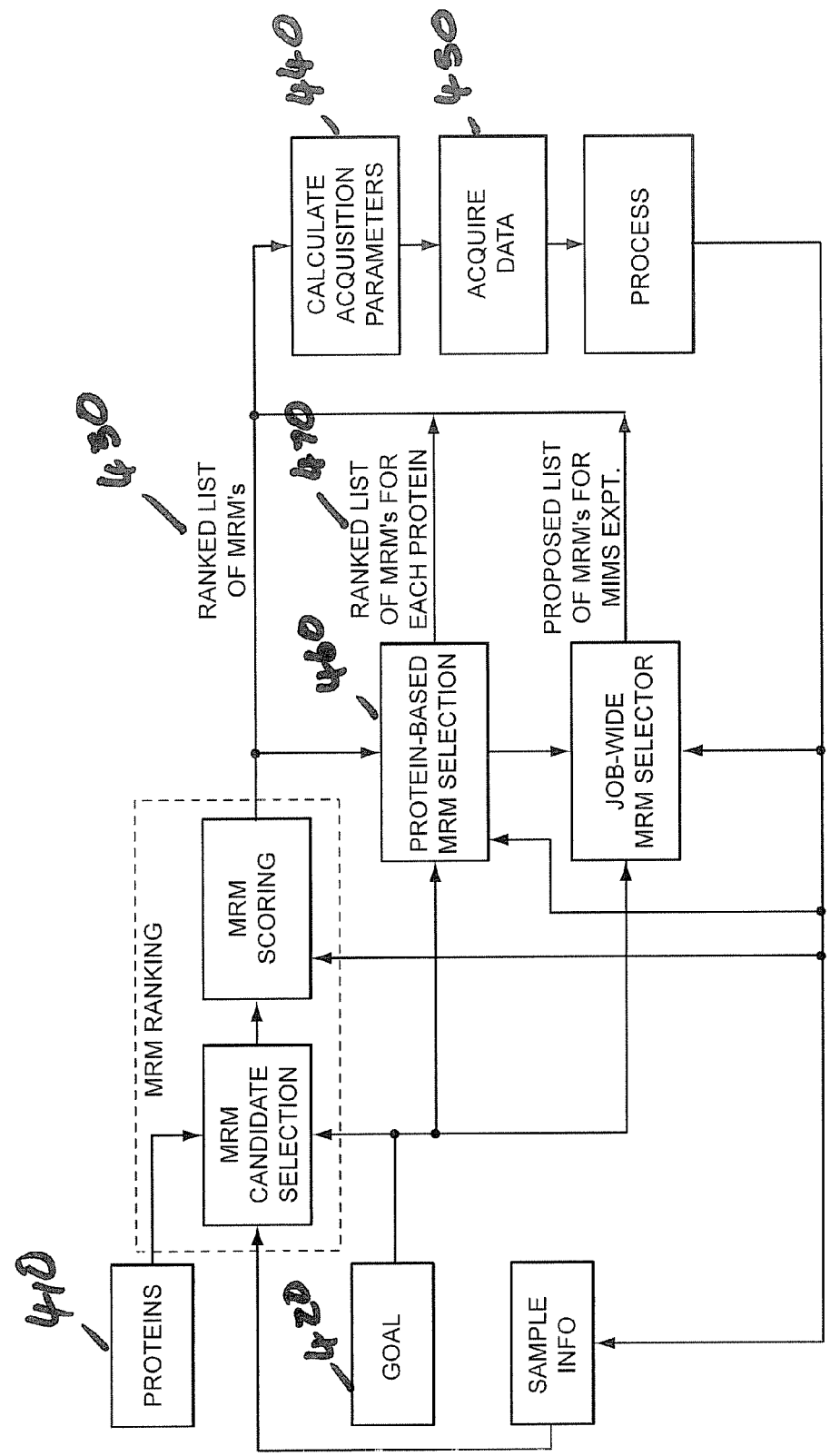
FIG. 4 is a flowchart describing an embodiment of the present teachings.

As illustrated in FIG. 4, the present teachings also provide for automation of the entire process to maximize experimental efficiency. In various embodiments, a ranked list of protein targets (410) is provided to software embodying the present teachings along with experimental constraints and goals (420) and information about the samples, which results in a selection of the MRMs with the highest probably of successfully identifying the protein targets (430). The software then generates a series of optimized MS/MS acquisition methods based on the characteristics of the mass spectrometer used (440) to detect the proteins of interest. As data is acquired from each run (450), database search results (confirming or denying peptide identities for PDITPs so far) are be fed back into the software (460) permitting further refinement of methods such as re-ranking the best PDITPs or removing failing PDITPs entirely (470). This can result in a final experimental design consisting of high quality, high sensitivity, confirmed PDITPs for a set of target proteins.

The present teachings also provide for learning from data. For example, as more information comes available in the design of PDITPs for peptides, this information can be learned and incorporated into the software as part of a set of soft decisions. This information could be in the form of theoretical models. It could also be an empirical model based on MS/MS data from instruments that have similar fragmentation patterns. The accumulation of empirical data to guide the models could itself be built into the computation done automatically for the user.

The present teachings provide several advantages such as the following. (1) Often samples are available in very little quantities and the most must be made out of every sample run. By applying rules and probabilities in the generation of PDITP scans, the maximum number of PDITPs can be utilized in every PDITP directed MS/MS experiment on every sample to improve efficiency. More proteins and more modifications can be hypothesized and tested in every run. (2) By prioritizing the list of PDITPs based on those combinations of features that will have the highest probabilities, the highest potential quality PDITPs will be used in the MIDAS method. This can enhance the discovery of PTIMs and proteins in each sample. (3) Developing methods which consist of the highest probability and quality PDITPs can aid in the development of PDITP-based biomarker validation methods. (4) Software incorporating the present teachings to develop high quality PDITP transitions can be used in both a discovery workflow and validation workflow. In a discovery workflow, hypothesized peptides to target proteins can be detected and their identity confirmed by MS/MS. In a validation workflow, hypothesized peptides can still be detected and confirmed but the goal is not an ID but a solid PDITP transition to be used downstream in a high throughput quantitative validation assay. (5) Experimental goals can be built into the design as well. For examples, if a user wants to perform isoform-specific quantitation of proteins, PDITP transitions must be developed to peptides that are not shared between proteins. Therefore, these transitions can be prioritized above the other peptides. The present teachings can be used where a user desires high confidence protein ID with MIDAS. In this case, it may be desirable, to identify as many peptides per protein as possible, rather than mainly the peptides that distinguish the proteins. The present teachings can be used for the discovery of phosphorylation sites. For example, when a consensus sequence for the sites of interest is known, PDITPs to these peptides can be prioritized, e.g. Ser/Thr/Tyr residue containing peptides are the next most important, then non-phosphorylated peptides might be added at the lowest priority to add sequence coverage to the experiment.

The following are examples of proteomics applications that can make use of the present teachings. (1) In targeted detection and confirmation of post-translational modifications workflows, proteins of interest have often already been identified by various means and the next step is to characterize the PTMs. The present teachings can be used to create PDITP scans to detect potential modified peptides of proteins of interest. Additional information specific to post-translation modifications such as consensus sequence information for the modification of interest can be used in addition to the above stated information to prioritize the list of PDITPs. (2) In a targeted detection and confirmation of proteins/biomarkers application, often, the protein has not yet been detected in the complex sample but it is hypothesized to be present. Alternatively, some very weak protein ID evidence may suggest a proteins/biomarkers' presence but more evidence is necessary to confirm the identification. As above, the protein sequence can be obtained from the protein sequence database and be used to generate PDITP scans for potential peptides of the protein in silico. (3) The present teachings can also be used in the development of quantitative PDITP-based validation methods in the absence of standards where the putative biomarker is hypothesized, For example MRM scans can be designed using the present teachings, and once the biomarker is detected and confirmed with MS/MS, then the best PDITP(s) are chosen from the set of detected peptides for the validation assay. When a standard protein/peptide is available, it can be used to develop high quality PDITPs and optimize the LC conditions. However, these standards are often not available or the synthesis of large numbers of standards becomes too expensive. At the biomarker validation stage, many putative biomarkers may need to be studied to determine the most diagnostic/predictive combination of biomarkers. (4) The MIDAS workflow (Applied Biosystems, Foster City, Calif.) provides quality control in certain environments. If the potential contaminations or by-products can be predicted or hypothesized, PDITP driven MS/MS acquisition can be constructed to monitor for these at high sensitivity and specificity. The resulting MS/MS can then be used to confirm or refute the detected contaminant, so that steps to minimize contamination can be taken.

Some embodiments incorporate feedback loops. Examples of a feedback loops to answer specific questions are as follows. Does MS/MS ID the right protein? Is there a better Y-ion for a MRM, based on looking at the full scan MS/MS? Which PDITP gives the best S/N? Which peptides to which proteins provide the best PDITP detection, elute over a time range? Specificity of PDITP, good S/N and no other significant chromatographic area in XIC. If replicates are run, which PDITPs to which peptides give the best confidence values? As discussed previously, questions such as these can be used in automated methods to assist is selecting the best PDITPs in a fashion similar to FIG. 4.

EXAMPLES

Example 1

Scoring of Parent-Daughter Ion Transition Pairs

This example demonstrates the probabilistic consideration of several factors in scoring PDITPs. In this example the factors considered pertain to the probability of the transition producing signal suitable for quantitation.

Probability of Detection

For a particular transition to be detected with quantifiable signal, a set of events must occur. These events (with associated probabilities) are:

The protein is present in the sample.
   1. Probability: P(protein present)

The protein is cleaved so as to produce the predicted peptide.
   2. Probability: P(expected cleavage|protein present)
   3. If (1) and (2) occur, the expected peptide is present in the sample.

The peptide ionizes to the charge state used to calculate the Q1 m/z.
   4. Probability: P(expected peptide ionization|peptide present)
   5. If (1)-(3) occur, the expected peptide is found using the predicted Q1 value.

The peptide produces the expected fragment.
   6. Probability: P(expected fragmentation|expected Q1)*P(expected peptide ionization )
   7. If (1)-(4) occur, the expected peptide fragment is present.

The fragment forms with the expected charge state. For simplicity, in this example only singly-charged fragments are focused on.
   8. P(expected fragment charge)=P(expected fragment charge|expected fragment)*P(expected fragment)
   9. If (1)-(5) occur, the expected ion from the peptide fragment is detected, meaning that the protein is successfully detected using this transition.

A probability can be ascribed to each of the statements above.

In this example PDITPs are scored by calculating the probability of the transition being detected, with the assumption that the protein is present in the sample (ie. calculate the probability that statements 2-5 are true.)

$P$(transition quantifiably detected|protein present)=

$P$(expected cleavage|protein present)*

$P$(expected peptide ionization|peptide present)*

$P$(expected fragmentation|expected $Q1$)*

$P$(expected fragment ionization|expected fragment)

Experimental Data

In this example a mixture of 20 proteins (at varying concentrations) Cys-alkylated with carboxamidomethyl are digested with trypsin. Approximately 150 PDITPs were generated for one of the proteins. A probability of detection was calculated for each transition.

Individual Event Probabilities

Below are descriptions of the calculation of individual event probabilities. Note that there are many alternate ways to calculate these, and the concept of joint consideration of these event probabilities is not limited to these specific methods of estimating event probabilities.

Protein Cleavage

Protein cleavage probabilities are determined based on the two residues between which cleavage is posited. The probabilities are stored in a 20-by-20 matrix, where the value in the i-th row and j-th column is the probability of cleavage of the C-terminal to the i-th amino and N-terminal to the j-th amino acid.

The matrix of cleavage probabilities for tryptic cleavage was generated using the following rules:

$P$(cleavage $C$-term to $R$)=0.9

$P$(cleavage $C$-term to $K$)=0.8

$P$(cleavage $N$-term to $P$)=0.05 (even when the $P$ is $C$-term to $R$ or $K$)

$P$(cleavage at any other site)=0

$P$(no cleavage)=1−$P$(cleavage)

The probability of expected cleavage for a peptide is calculated as the probability of getting both the two terminal cleavage events and no cleavage within the proposed peptide sequence.

$$P(\text{Expected\_cleavage}) = P(\text{cleavage\_at\_N-term}) P(\text{cleavage\_at\_C-term}) \prod_{i=1}^{L-1} P(\text{no\_cleavage}_{i,i+1})$$

where L is the length of the peptide sequence, and no_cleavage$_{i,i+1}$ represent the event of no cleavage occurring between the i-th and (i+1)-th amino acids within the peptide sequence.

Peptide Ionization

Electrospray ionizaiton was employed with H+ as the adduct ion. With this ionization basic sites tend to take on the H+ adduct. The amino acids Arg, Lys and His are basic, and the peptide N-terminus tends to be a basic site as well. With that in mind, a reasonable prediction of peptide charge is:

Charge(sequence)=# of basic amino acids in sequence+1

A review of high confidence peptide identifications showed that this charge prediction is often but not always true. When the prediction was observed to be wrong it was high by one charge. Based on the observations, the following probabilities were used for peptide ionization:

$P$(charge=# of basic residues+1)=0.65

$P$(charge=# of basic residues)=0.35

Peptide Fragmentation

A measure of fragmentation probabilities was approximated using the data collected and segmented via a mobile proton model (Kapp et al (2003) Anal Chem 75(22), 6251.) In the model, peptides are classified as mobile, partially mobile or non-mobile based on their sequence and charge. The paper includes an analysis of fragment abundance for each class of peptide and the N-terminal and C-terminal side of each residue. This fragment abundance for a particular fragmentation site relative to average fragmentation abundance is referred to as the Cleavage Intensity Ratio (CIR).

$P$(expected fragmentation)=2^(average CIR)/(2^(averageCIR)+1), where averageCIR is given by averageCIR=(C-term CIR of amino acid on N-term side+N-term CIR of amino acid on C-term side)/2;

The following heuristic formula was used to estimate fragment probabilities:

For example, for the sequence 'AAGGTLNR', the b2 and y6 ions form by fragmentation between the A and G, so the posited fragmentation site is on the C-terminal of A and the N-terminal side of G, so averageCIR is the average of the CIR for fragmentation C-terminal to A and the CIR for fragmentation N-terminal to G.

Peptide Fragment Charge

In the example only singly-charged fragments were monitored (though extending the concept to other fragment charges is straightforward). The probability of a fragment being singly-charged was estimated based on the number of basic amino acids in the fragment. Fragments with at least one basic amino acid are more likely to have some charge. Fragments without a basic amino acid are more likely to be neutral, and hence not detected at all by the second mass analyzer.

$P$(fragment singly-charged|fragment has one or more basic amino acids)=0.9

$P$(fragment singly-charged|fragment has no basic amino acids)=0.2

FIG. 5 lists 293 transitions generated for the protein Fructose-Bisphosphate according to Example 1, and their respective probabilities of detection.

Figure 6:
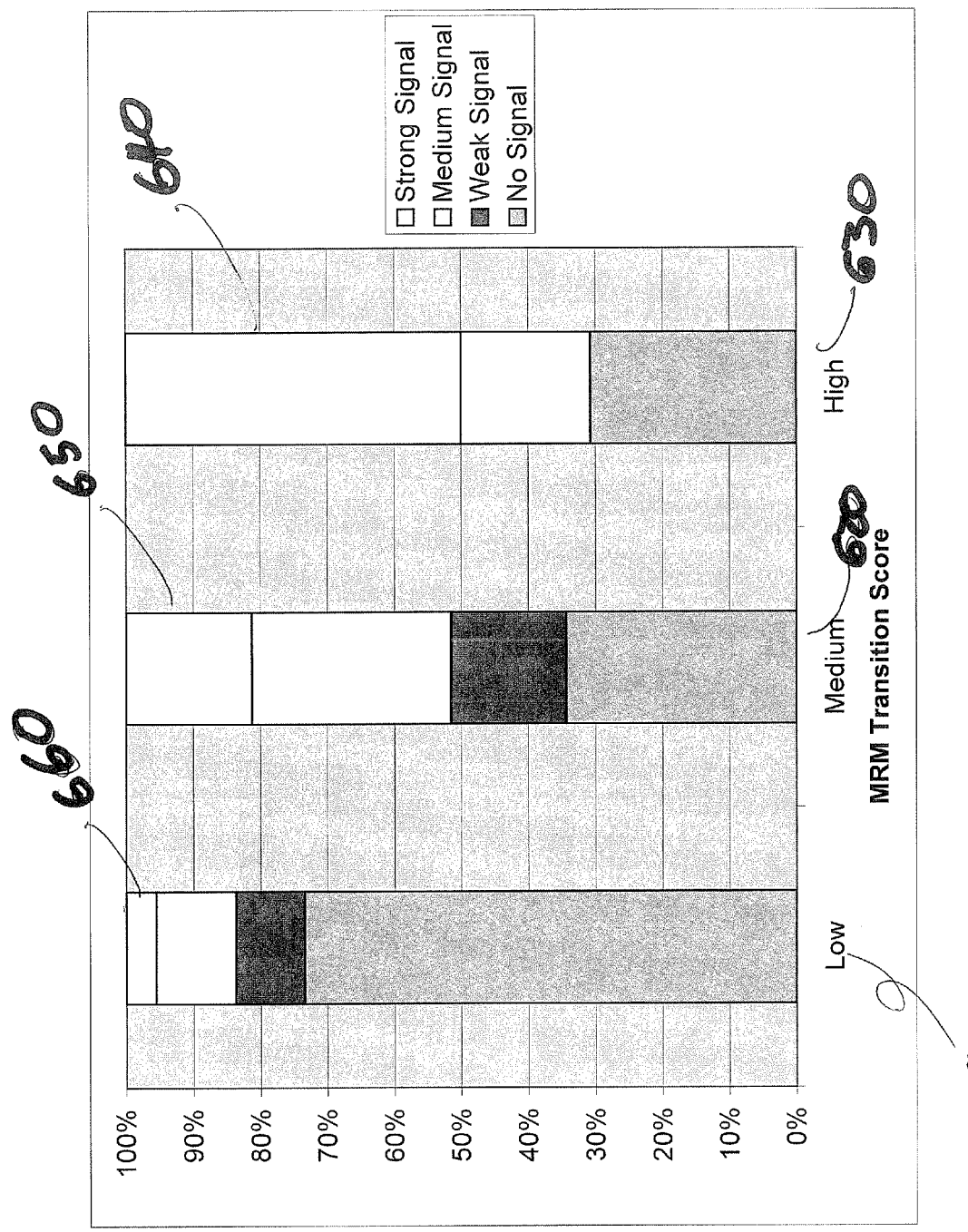
FIG. 6 shows results confirming that the present teachings accurately predict a PDITP's utility for MRM experiments.

FIG. 6 shows that higher scoring MRM transitions predicted by the present teachings produced more intense signals. The figure was generated by binning MRM transitions into 3 classes of score, Low (610) with a score<0.05, Medium (620) with a score between 0.05 and 0.15 (620) and High (630) with a score above 0.15. The observed MRM transition peak areas were clustered into 4 classes as indicated in the legend. These are No Signal, Weak Signal (peak area<1e4), Medium Signal (1e4<=peak area<1e5) and Strong Signal (peak area>=1e5). The results show that by far the highest proportion of intense PDITPs (640) occurred in bin 630. The next highest proportion of strong-signal PDITP occurred in bin 650, and finally only a very small proportion of strong-signal PDITPs occurred in bin 660.

Example 2

Predicting Interference from a Sequence Database

It is possible to generate an exhaustive list of possible parent-daughter transitions given a sequence database, protein cleavage rules and peptide modifications, but not all of these theoretical transitions are equiprobable. For PDITP-X to interfere with PDITP-Y, the following events must occur:
1. The interfering protein or other component is present in the sample.
   Probability: P(protein present)
2. The interfering protein is cleaved so as to produce the predicted peptide.

Probability: P(expected cleavage|protein present)

If (1) and (2) occur, the expected peptide is present in the sample.

3. The interfering peptide ionizes to the charge state used to calculate the Q1 m/z.

Probability: P(expected peptide ionization|peptide present)

If (1)-(3) occur, the expected peptide is found using the predicted Q1 value.

4. The interfering peptide produces the expected fragment with sufficient intensity to interfere.

Probability: P(expected fragmentation|expected Q1)*P(expected peptide ionization)

If (1)-(4) occur, the expected peptide fragment is present.

5. The interfering fragment forms with the expected charge state.

P(expected fragment charge)=P(expected fragment charge|expected fragment)*P(expected fragment)

If (1)-(5) occur, the expected ion from the peptide fragment is detected, meaning that the protein is successfully detected using this PDITP.

Probability of Sufficient Intensity to Interfere

In various embodiments, given a number of potentially interfering PDITPs, and the probability density function for the intensity of each, a probability density function for the degree of total interference is calculated as follows.

$$p(\text{Transition intensity}) = p(\text{protein abundance}) * P(\text{cleavage}) * \\ P(\text{mods}) * P(\text{ionization to required charge}) * P(\text{transmission through targeted } Q1 \text{ m/z}) * P(\text{expected fragmentation}) * P(\text{fragment charge}) * P(\text{trasmission through targeted } Q3 \text{ m/z})$$

Where p(x) is a probability density function for the variable x, and P(y) is the probability of event y.

Transmission Windows

The terms:

$P(\text{transmission through targeted Q1 m/z})$ $P(\text{transmission through targeted Q3 m/z})$ relate to the fact that an PDITP need not have identical Q1 and Q3 m/z values as another PDITP to cause interference. Q1 and Q3 will pass ions through in a narrow m/z window surrounding the targeted m/z values, however, the percentage of ions transmitted generally decreases as m/z deviates further from the targeted value. Various embodiments approximate a model for the transmission window based on the observation that the window is an asymmetric Gaussian, with a smaller standard deviation to the left of the target value than to the right.

Leveraging Past MS Data

Of the terms needed to predict a transition's intensity, the least well known are typically:

$p(\text{protein abundance})$, and $P(\text{ionization to required charge})$

In various embodiments, where a MRM analysis is to be performed on samples already extensively analyzed by global MS analysis, the list of detected proteins is leveraged to help. For example, instead of modeling protein abundance using an estimate of the distribution of protein abundances, various embodiments split the distribution into two parts, a (typically small) distribution of higher abundance proteins used to characterize those found in a global MS analysis, and a (typically large) distribution of lower abundance proteins used to characterize those not found in global MS analysis. A similar technique can be used for peptides, where peptides found in prior analysis are assumed to be more intense.

Aggregating "Interfering" PDITPs

The mere theoretical existence of interfering transitions is not enough to compromise the efficacy of a PDITP for monitoring a protein. Any signal measurement obtained through an MRM scan will have some noise and possibly some interference. The key is to make sure that the signal quality is acceptable, as measured by the S/(N+I) ratio (signal to noise plus interference). As an approximation, the noise can be treated as negligible and the S/I ratio simply assessed as sufficiently high. The total impact of a set of interfering PDITPs can be calculated via several means, including:

convolution to calculate the probability density function for the total interference, treating the probability density functions for each interferer's intensity as normally distributed, and simply adding the means and taking the quadrature sum of the standard deviations to characterize the distribution of total interference intensity.

Example 3

Estimating Chance of Interference Without a Sequence Database

The specificity of a transition can also be approximated based on the length of the peptide sequence and the length of the fragment sequence.

The chance of interference of a randomly-generated transition from a random peptide of the same length is approximately $P(\text{interference})=P(Q1 \text{ comes from transposition of same sequence})*$ $P(Q3 \text{ comes from transposition of same sequence})$ This formula results in favoring PDITPs from long sequence parents to daughter ions from near the midpoint of the sequence. Daughter ions near either end of the ladder have the least specificity, because for fixed N, N-choose-k is highest at k near N/2.

The invention claimed is:

1. A non-transitory computer readable medium containing instructions for controlling a computer system to perform a method for ranking parent daughter ion transition pairs (PDITPs), the method comprising:
receiving a target protein;
determining one or more peptides that would result from cleavage of the target protein;
determining one or more fragments that would result from subjecting the one or more peptides to a fragmentation experiment in a mass spectrometer;
forming one or more PDITPs from the one or more fragments, where each PDITP comprises a daughter ion and its corresponding parent ion;
calculating for each PDITP of the one or more PDITPs a probability of detection from a probability of one or more variables that relate a peptide of the each PDITP to the target protein and a probability of one or more variables that relate a fragment ion of the each PDITP to the peptide using the MRM scoring module;
receiving at least one goal for the experiment;
calculating for each PDITP of the one or more PDITPs a probability that the each PDITP is useful for the at least one goal;
calculating a joint probability for each PDITP of the one or more PDITPs from the probability of detection and the probability that the each PDITP is useful for the at least one goal; and
ranking the one or more PDITPs based on the joint probability.

2. The computer readable medium of claim 1, further comprising calculating parameters of an acquisition method for at least one of the highest ranked PDITPs of the one or more PDITPs and performing the acquisition method on the mass spectrometer.

3. The computer readable medium of claim 2, wherein the parameters comprise one or more of a collision energy parameter, an ionization parameter, or a transmission parameter.

4. The computer readable medium of claim 2, further comprising receiving data from the spectrometer after the mass spectrometer performs the acquisition method, searching a database to confirm a peptide identity for a at least one PDITP, and re-ranking the one or more one or more PDITPs based on the search.

5. The computer readable medium of claim 1, wherein the one or more variables that relate a peptide of the each PDITP to the target protein and the one or more variables that relate a fragment ion of the each PDITP to the peptide comprise one or more of a charge state, a molecular weight, a detection in previous mass spectrometry data, an enzyme digestion specificity/efficiency, a mass spectrometry ionization efficiency, or signal strength.

6. The computer readable medium of claim 1, wherein the at least one goal comprises one of detecting differential expression between isoforms, detecting peptide modifications, identifying peptides, identifying proteins, or quantifying proteins.

7. The computer readable medium of claim 1, wherein calculating for each PDITP of the one or more PDITPs a probability that the each PDITP is useful for the at least one goal comprises calculating a probability for one or more measurements related to the at least one goal.

8. The computer readable medium of claim 7, wherein the one or measurements comprise one or more of a measurement specific to a particular isoform, a specificity measurement, a peptide uniqueness measurement, or a measurement of normalization peptides.

9. A system for ranking parent daughter ion transition pairs (PDITPs), the system comprising:
a mass spectrometer; and
a processor that receives a target protein,
determines one or more peptides that would result from cleavage of the target protein,
determines one or more fragments that would result from subjecting the one or more peptides to a fragmentation experiment in the mass spectrometer,
forms one or more PDITPs from the one or more fragments, where each PDITP comprises a daughter ion and its corresponding parent ion,
calculates for each PDITP of the one or more PDITPs a probability of detection from a probability of one or more variables that relate a peptide of the each PDITP to the target protein and a probability of one or more variables that relate a fragment ion of the each PDITP to the peptide,
receives at least one goal for the experiment,
calculates for each PDITP of the one or more PDITPs a probability that the each PDITP is useful for the at least one goal,
calculates a joint probability for each PDITP of the one or more PDITPs from the probability of detection and the probability that the each PDITP is useful for the at least one goal, and
ranks the one or more PDITPs based on the joint probability.

10. The system of claim 9, wherein the processor calculates parameters of an acquisition method for at least one of the highest ranked PDITPs of the one or more PDITPs and the mass spectrometer performs the acquisition method.

11. The system of claim 10, wherein the parameters comprise one or more of a collision energy parameter, an ionization parameter, or a transmission parameter.

12. The system of claim 10, wherein the processor receives data from the spectrometer after the mass spectrometer performs the acquisition method, searches a database to confirm a peptide identity for a at least one PDITP, and re-ranks the one or more one or more PDITPs based on the search.

13. The system of claim 9, wherein the one or more variables that relate a peptide of the each PDITP to the target protein and the one or more variables that relate a fragment ion of the each PDITP to the peptide comprise one or more of a charge state, a molecular weight, a detection in previous mass spectrometry data, an enzyme digestion specificity/efficiency, a mass spectrometry ionization efficiency, or signal strength.

14. The system of claim 9, wherein the at least one goal comprises one of detecting differential expression between isoforms, detecting peptide modifications, identifying peptides, identifying proteins, or quantifying proteins.

15. A method for calculating a probability of detection for ranking parent daughter ion transition pairs (PDITPs), the method comprising:
receiving a target protein using a processor;
determining one or more peptides that would result from cleavage of the target protein using the processor;
determining one or more fragments that would result from subjecting the one or more peptides to a fragmentation experiment in a mass spectrometer using the processor;
forming one or more PDITPs from the one or more fragments using the processor, where each PDITP comprises a daughter ion and its corresponding parent ion;
calculating for each PDITP of the one or more PDITPs a probability of detection from a probability of one or more variables that relate a peptide of the each PDITP to the target protein and a probability of one or more variables that relate a fragment ion of the each PDITP to the peptide using the processor, receiving at least one goal for the experiment using the processor;

calculating for each PDITP of the one or more PDITPs a probability that the each PDITP is useful for the at least one goal using the processor;

calculating a joint probability for each PDITP of the one or more PDITPs from the probability of detection and the probability that the each PDITP is useful for the at least one goal using the processor; and ranking the one or more PDITPs based on the joint probability using the processor.

16. The method of claim 15, wherein the one or more variables that relate a peptide of the each PDITP to the target protein and the one or more variables that relate a fragment ion of the each PDITP to the peptide comprise one or more of a charge state, a molecular weight, a detection in previous mass spectrometry data, an enzyme digestion specificity/efficiency, a mass spectrometry ionization efficiency, or signal strength.

17. The method of claim 15, wherein the at least one goal comprises one of detecting differential expression between isoforms, detecting peptide modifications, identifying peptides, identifying proteins, or quantifying proteins.

* * * * *